United States Patent
Sharaf et al.

(10) Patent No.: US 10,196,680 B2
(45) Date of Patent: *Feb. 5, 2019

(54) METHODS OF DETECTING TARGET NUCLEIC ACIDS

(71) Applicant: APPLIED BIOSYSTEMS, LLC, Carlsbad, CA (US)

(72) Inventors: Muhammad A. Sharaf, Oakland, CA (US); Timothy Woudenberg, San Francisco, CA (US); Khairuzzaman Bashar Mullah, Union City, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,606

(22) Filed: Jun. 5, 2017

(65) Prior Publication Data

US 2017/0275678 A1    Sep. 28, 2017

Related U.S. Application Data

(63) Continuation of application No. 15/241,711, filed on Aug. 19, 2016, now Pat. No. 9,677,126, which is a continuation of application No. 14/790,369, filed on Jul. 2, 2015, now Pat. No. 9,434,982, which is a continuation of application No. 14/137,376, filed on Dec. 20, 2013, now Pat. No. 9,074,252, which is a continuation of application No. 13/590,794, filed on Aug. 21, 2012, now Pat. No. 8,637,247, which is a continuation of application No. 11/685,189, filed on Mar. 12, 2007, now abandoned.

(60) Provisional application No. 60/781,780, filed on Mar. 12, 2006.

(51) Int. Cl.
| | |
|---|---|
| C12Q 1/68 | (2018.01) |
| C12Q 1/6825 | (2018.01) |
| C12Q 1/6816 | (2018.01) |
| C12Q 1/6876 | (2018.01) |
| C12Q 1/6823 | (2018.01) |
| C12Q 1/6827 | (2018.01) |
| C12Q 1/6832 | (2018.01) |
| G01N 27/447 | (2006.01) |

(52) U.S. Cl.
CPC ......... *C12Q 1/6825* (2013.01); *C12Q 1/6816* (2013.01); *C12Q 1/6823* (2013.01); *C12Q 1/6827* (2013.01); *C12Q 1/6832* (2013.01); *C12Q 1/6876* (2013.01); *G01N 27/44726* (2013.01); *G01N 27/44791* (2013.01)

(58) Field of Classification Search
None
See application file for complete search history.

(56) References Cited

U.S. PATENT DOCUMENTS

| | | | |
|---|---|---|---|
| 6,350,580 | B1 | 2/2002 | Sorge |
| 6,723,513 | B2 | 4/2004 | Lexow |
| 8,637,247 | B2 | 1/2014 | Sharaf et al. |
| 9,074,252 | B2 | 7/2015 | Sharaf et al. |
| 9,434,982 | B2 | 9/2016 | Sharaf et al. |
| 9,677,126 | B2 | 6/2017 | Sharaf et al. |
| 2001/0036632 | A1 | 11/2001 | Yu et al. |
| 2002/0142344 | A1* | 10/2002 | Akeson ............... C12Q 1/6823 435/7.1 |
| 2002/0197618 | A1 | 12/2002 | Sampson |
| 2003/0022167 | A1 | 1/2003 | Alsmadi et al. |
| 2006/0210995 | A1 | 9/2006 | Joyce |
| 2006/0263789 | A1* | 11/2006 | Kincaid ................ C12Q 1/68 435/6.12 |
| 2007/0190543 | A1 | 8/2007 | Livak |
| 2010/0291548 | A1 | 11/2010 | Sharaf et al. |

FOREIGN PATENT DOCUMENTS

| | | |
|---|---|---|
| WO | 2001/081896 | 11/2001 |
| WO | 2007/117832 | 10/2007 |

OTHER PUBLICATIONS

PCT/US2007/063828, International Search Report and Written Opinion, dated Nov. 25, 2008, 1-6.

\* cited by examiner

*Primary Examiner* — James Martinell

(57) ABSTRACT

The present disclosure relates to methods of identifying target nucleic acids by using coded molecules and its analysis by translocation through a nanopore. Generally, coded molecules are subject to a target polynucleotide dependent modification. The modified coded molecule is detected by isolating the modified coded molecules from the unmodified coded molecules prior to analysis through the nanopore or by detecting a change in the signal pattern of the coded molecule when analyzed through the nanopore.

6 Claims, 5 Drawing Sheets

METHODS OF DETECTING TARGET NUCLEIC ACIDS

1. CROSS-REFERENCE TO RELATED APPLICATIONS

Figure 1A:
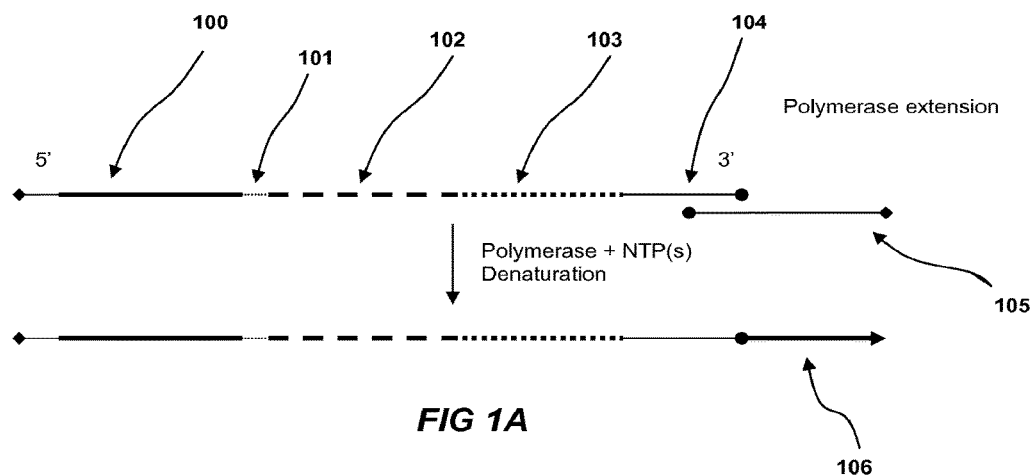

This application is a continuation of U.S. application Ser. No. 15/241,711 filed Aug. 19, 2016, which is a continuation of U.S. application Ser. No. 14/790,369 filed Jul. 2, 2015, which is a continuation of U.S. application Ser. No. 14/137,376 filed Dec. 20, 2013, which is a continuation of U.S. application Ser. No. 13/590,794 filed Aug. 21, 2012, which is a continuation of U.S. application Ser. No. 11/685,189 filed Mar. 12, 2007, which claims the benefit under 35 U.S.C. § 119(e) of U.S. Provisional Application No. 60/781,780 filed Mar. 12, 2006. The entire contents of the aforementioned applications are incorporated by reference in their entirety.

2. BACKGROUND

The detection of target nucleic acids has many critical applications in medicine, forensics, and environmental monitoring. To provide consistency, speed, and specificity in detecting multiple target polynucleotides, various mutiplexing techniques have been developed in which detection is carried out in a single reaction. Multiplexing approaches based on microarrays and microbeads combine powerful nucleic acid amplification strategies with the massive screening capability to provide highthroughput capacity along with high level of sensitivity, specificity, and consistency.

Micoarrays and microbeads are particularly suited for detecting single nucleotide polymorphisms, which represents one of the largest sources of diversity in the genome of organisms. Some single nucleotide variations are directly linked to phenotypic traits of interest, such as a disease or disease susceptibility. Most single nucleotide polymorphisms, however, are neutral. But because most biological processes involve the interaction of a multitude of genes, even neutral sequence variations serve as useful markers in linkage maps for studying phenotypes having an underlying multigenic basis. The growing number of SNPs, for example the SNP database maintained by the National Center for Biotechnology Information (NCBI), provide a rich resource for genetic analysis based on sequence polymorphisms.

Despite the advances of microarray and microbead based nucleic acid detection systems, these methods still have drawbacks. For example, the need to amplify the target nucleic acid in many applications represents a disadvantage because of variability in amplification efficiency. Since microarray and microbead techniques typically compare signal intensity between samples for determining a positive or negative result, variability in amplification reactions can adversely affect the determination of the presence or absence of a particular target nucleic acid in these assay formats. Moreover, microarray and microbead based detection typically rely on summing of signals from a population of probe-target nucleic acid interactions, which limits the sensitivity of the assays.

In view of the foregoing, it is desirable to have alternative techniques for detecting nucleic acids, where the detection technique is less susceptible to variation in amplification efficiency, displays a high level of sensitivity, and is adaptable for multiplexing reactions to detect SNPs.

3. SUMMARY

The present disclosure relates to use of nanopores to detect target polynucleotides. The methods involve use of coded molecules having an associated target probe that specifically recognizes a target polynucleotide; modifying the coded molecule with a modifying agent, where the modification is dependent on presence of the target polynucleotide; and detecting the modified coded molecule by translocating it through a nanopore.

Generally, the method comprises contacting a coded molecule with a target polynucleotide, wherein the coded molecule comprises one or more block polymer regions and a target probe capable of hybridizing to the target polynucleotide. The mixture of coded molecule and the target polynucleotide is treated with a modifying agent that modifies the target probe if the target polynucleotide is hybridized to the target probe. In the absence of a hybridized target polynucleotide, the modification of the target probe, and thus modification of the coded molecule, does not occur efficiently. The coded molecule is then translocated through a nanopore and interrogated to detect a signal that is reflective of the polymer characteristics of the block polymer region. In some embodiments where there is a modification of the coded molecule, the modification can alter the signal pattern displayed by a coded molecule such that an altered signal pattern is indicative of the presence of the target polynucleotide. The detected signal pattern is also used to identify the specific coded molecule and its associated target probe, and thus the specific target polynucleotide detected. In some embodiments, the modified coded molecule can be isolated from unmodified coded molecules based on the target polynucleotide dependent modification, and the isolated coded molecule translocated through a nanopore to detect a signal pattern, which can then be associated to a specific coded molecule and therefore the specific target polynucleotide detected in the reaction.

In the present disclosure, the target probes are designed to hybridize to a target polynucleotide to form polynucleotide structures that can be modified by various modifying agents. In some embodiments, the target probe comprises a 3-prime region or segment that hybridizes to a 5-prime region of a target polynucleotide such that the hybridized 3-prime region of the target probe can serve as a primer for elongation by a template-dependent polymerase. In some embodiments, extension of the 3-prime region of the target probe can alter the signal pattern because of the polynucleotide segment added to the coded molecule by the template-dependent polymerase. Because the extension does not occur in the absence of a template, changes to the signal pattern can occur only in the presence of the target polynucleotide. In some embodiments, the target polynucleotide is a circular polynucleotide formed by ligation of an open circle probe, where the open circle probe is efficiently ligated to form the circular target polynucleotide only in the presence of a nucleic acid of interest. Elongation of the target probe by replication of the circular polynucleotide provides a basis for determining the presence or absence of circular polynucleotide, and thus the presence or absence of the nucleic acid of interest.

In some embodiments, the method further comprises hybridizing a ligation probe to the target polynucleotide, where the ligation probe and the target probe hybridize to adjacent regions on the target polypeptide such that the hybridized ligation probe and target probe are suitable substrates for a ligase. Treatment with a ligase results in ligation of the ligation probe to the target probe, thereby structurally modifying the coded molecule. A change in the detected signal pattern, as compared to the signal pattern of an unmodified coded molecule, indicates the presence of the target polynucleotide. In some embodiments, the ligation probe can further comprise a signal generating segment, which is a polymer segment that can change the signal pattern of the coded molecule. In other embodiments, the ligation probe comprises a capture tag, which allows the ligase-modified coded molecule to be isolated from unmodified coded molecules. In various embodiments, the ligation probe or the target probe can be used to interrogate a site of nucleotide sequence variation.

In some embodiments, the method further comprises hybridizing a FLAP probe to the target polynucleotide to form a FLAP structure recognized by a FLAP endonuclease and consequent cleavage of the target probe by a FLAP endonuclease. In these embodiments, the FLAP substrate comprises (a) a target polynucleotide, wherein the target polynucleotide comprises adjacent first and second regions, (b) a FLAP probe comprising a 3-prime segment that hybridizes to the first region, and (c) a target probe comprising a 5-prime region and a 3-prime region, where the 3-prime region hybridizes to the second region of the target polynucleotide. Hybridization of the FLAP probe and the target probe to the adjacent first and second regions on the target polynucleotide forms a FLAP substrate in which the target probe is cleaved by a FLAP endonuclease, thereby resulting in separation of the 5-prime region of the target probe from the coded molecule. In some embodiments, a change in the signal pattern arising from cleaving off of the 5-prime region of the target probe indicates the presence of the target polynucleotide. Use of target probes having a signal generating segment can assist in distinguishing unmodified coded molecules from FLAP-endonuclease modified coded molecules. In other embodiments, the target probe can have a capture tag, which is removed by action of the FLAP endonuclease, thus permitting isolation of FLAP-endonuclease modified coded molecules from unmodified coded molecules. In various embodiments, the FLAP probe or the target probe can be used interrogate a site of polynucleotide polymorphism to determine the presence or absence of a nucleotide sequence variation.

In some embodiments, the method comprises hybridizing a target probe to a target polynucleotide to form an endonuclease recognition site and a corresponding endonuclease cleavage site. In these embodiments, treating the hybridized target polynucleotide and the target probe with an endonuclease that specifically recognizes the recognition site results in cleavage of the target probe. In some embodiments, the endonuclease recognition site can be a sequence-specific endonuclease site while in other embodiments, the endonuclease recognition site can be a mismatch-specific endonuclease. Use of target probes having a signal generating segment can be used to distinguish unmodified coded molecules from endonuclease-modified coded molecules.

In some embodiments, a target probe is hybridized to the target polynucleotide to form a double stranded region in which the target probe is made susceptible to an exonuclease. Removal of all or a portion of the target probe alters the structure of the coded molecule, which can result in an altered signal pattern indicative of the presence of a specific target polynucleotide.

The present disclosure further provides multiplexed detection based on the methods described above. Detection of a plurality of different target polynucleotides can be carried out using subpopulations of coded molecules, i.e., a plurality of pluralities, where each subpopulation has a target probe that hybridizes to a specific target polynucleotide different from the target polynucleotide bound by the targets probes of the other subpopulations. Each member of a subpopulation of coded molecules can display a signal pattern that is distinguishable from coded molecules of other subpopulations. By detecting the signal pattern of a translocated coded molecule, the signal pattern can be associated to a specific coded molecule subpopulation, and thus the specific target polynucleotide detected in the assay.

Interrogation of the coded molecule following treatment with the modifying agent is carried out by translocating the coded molecule through a nanopore and detecting the signal pattern associated with the coded molecule. Various detection strategies are contemplated, including current blockade, electron tunneling current, and imaging of charge induced fields. The detected signal pattern is analyzed and associated to a specific coded molecule and its corresponding target probe.

The methods herein can be used to detect any target polynucleotide, such as polynucleotides associated with diseases and other medical conditions as well as polynucleotides with sequence variations useful for genotyping applications, such as forensic analysis, environmental sampling, and evolutionary studies.

Further provided herein are kits for the detection of target polynucleotides by the disclosed methods. Kits can contain coded molecules with target probes directed to various target polynucleotides, modifying agents for the modification of the coded molecules, and nanopore devices for detecting the coded molecules. In addition, the kits can contain various coded molecule standards for obtaining representative signal pattern profiles of unmodified coded molecules and representative signal pattern profiles of modified coded molecules for comparison of test samples. In various embodiments, the kits can also contain instructions on use of kit components and nanopore detection methodology, wherein the instructions can be in any medium used for disseminating such information, including, among others, printed medium, video tape, compact disc, flash memory devices, and computer disc.

4. BRIEF DESCRIPTION OF THE FIGURES

Figure 1B:
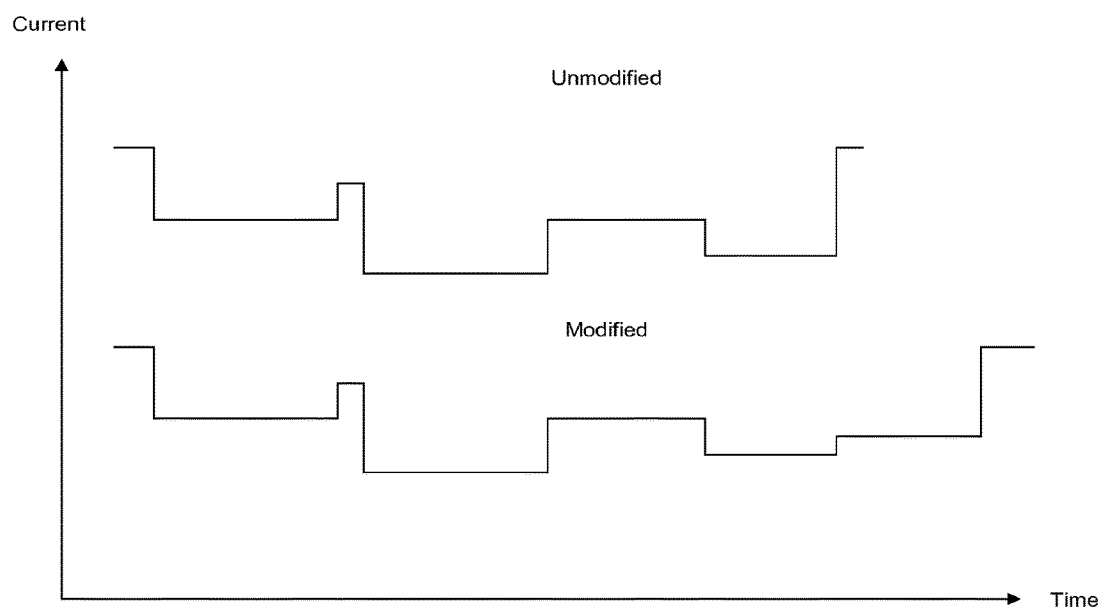

FIG. 1A is an illustration of a polymerase-mediated extension assay in which a coded molecule is modified by a template-dependent polymerase mediated extension of the 3-prime region or segment of the target probe hybridized to the target polynucleotide. The segments represented by (-) (- - - ), and ( . . . ) comprise block polymer regions. FIG. 1B symbolically illustrates a current blockade signal profile for an unmodified coded molecule and polymerase-modified coded molecule.

Figures 2A, 2B:
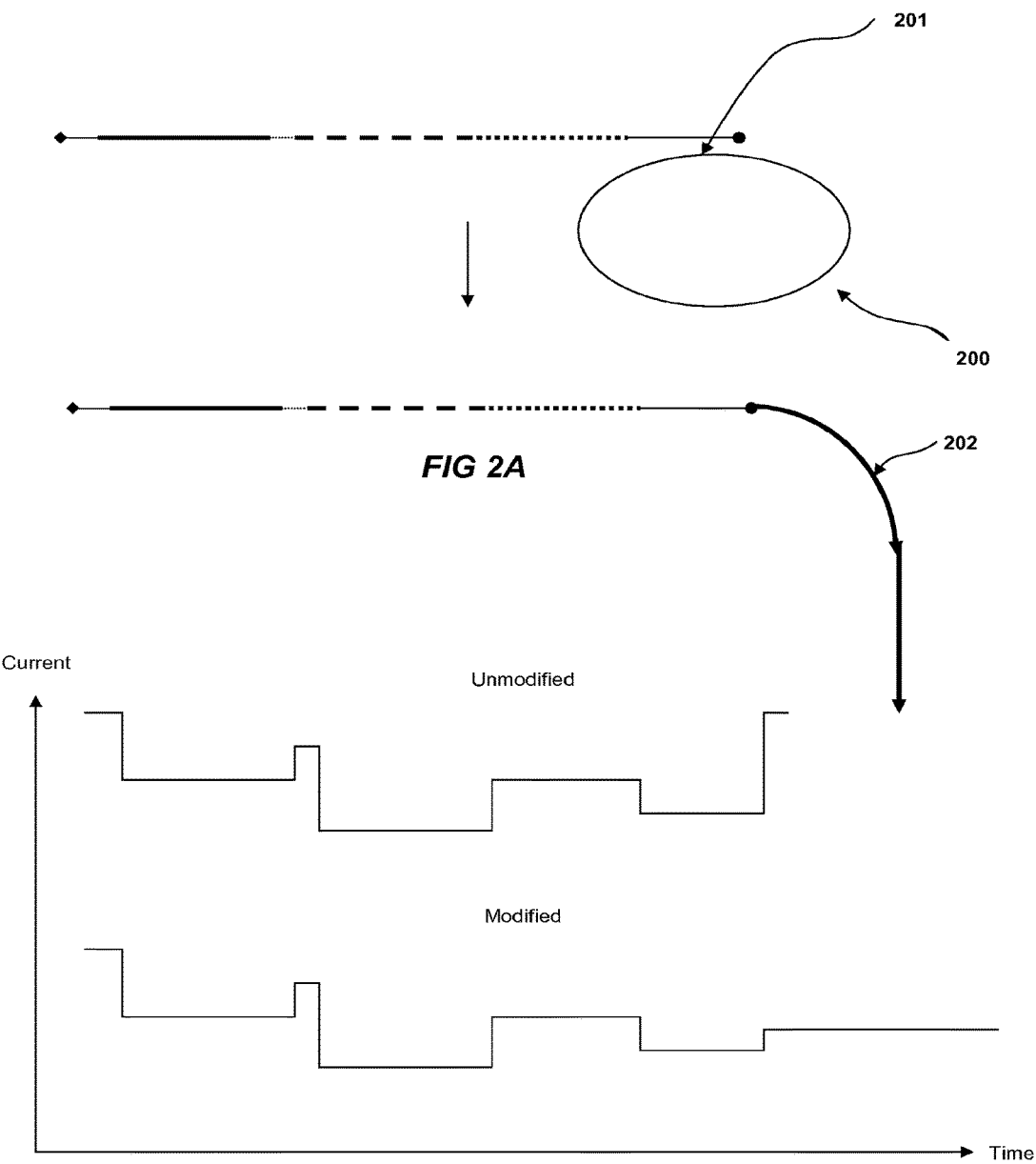

FIG. 2A is an illustration of a primer extension assay in which a target probe segment of the coded molecule hybridizes to a ligated open circle probe (OCP). Polymerase-mediated extension of the coded molecule results in a coded molecule with an extended 3-prime region or segment that can comprise multiple copies of the circular template. FIG. 2B symbolically illustrates a current blockade signal profile for an unmodified coded molecule and a polymerase-modified coded molecule.

Figure 3A:
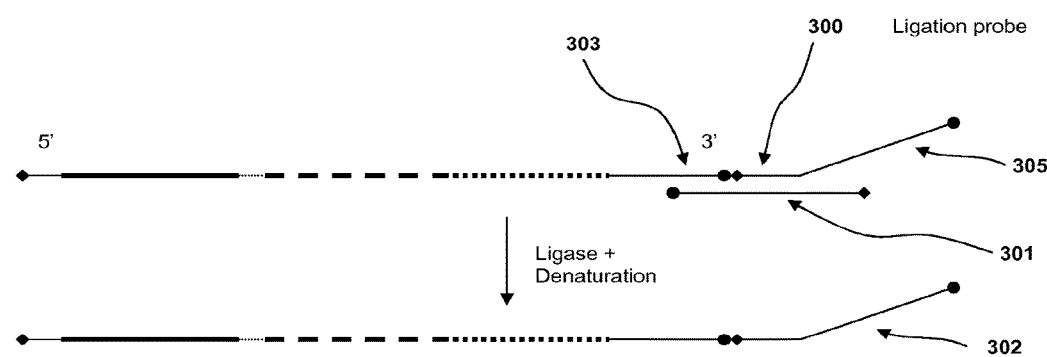
Figure 3B:
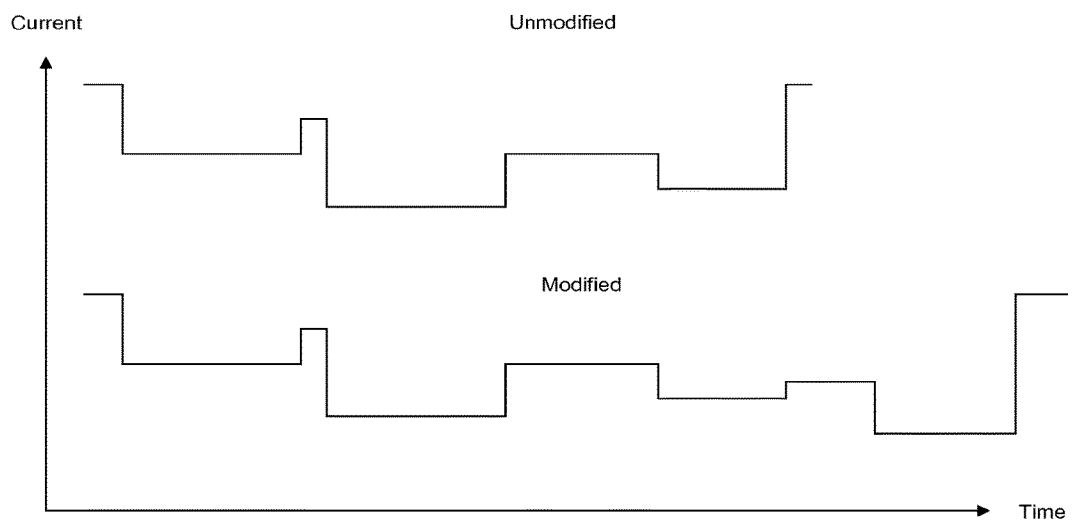

FIG. 3A is an illustration of a ligation assay in which a target probe of the coded molecule is ligated to a ligation probe. The target probe and the ligation probe are adjacently hybridized to a target polynucleotide to juxtapose the terminus of the target probe and ligation probe. Treatment with a ligase ligates the ligation probe to the target probe. In the illustrated embodiment, the ligation probe comprises a signal generating segment, which displays a unique current blockade signal profile. FIG. 3B symbolically illustrates a current blockade signal profile for an unmodified coded molecule and a coded molecule modified by ligation of a ligation probe.

Figure 4A:
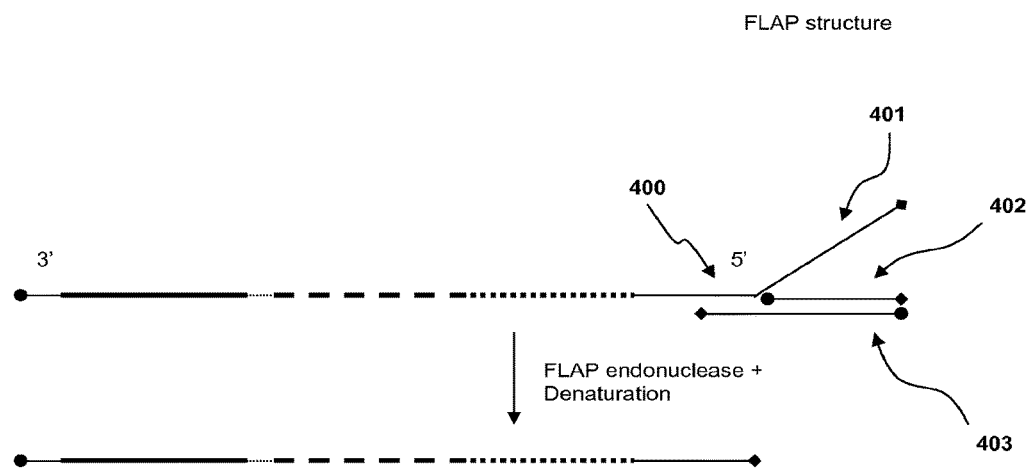
Figure 4B:
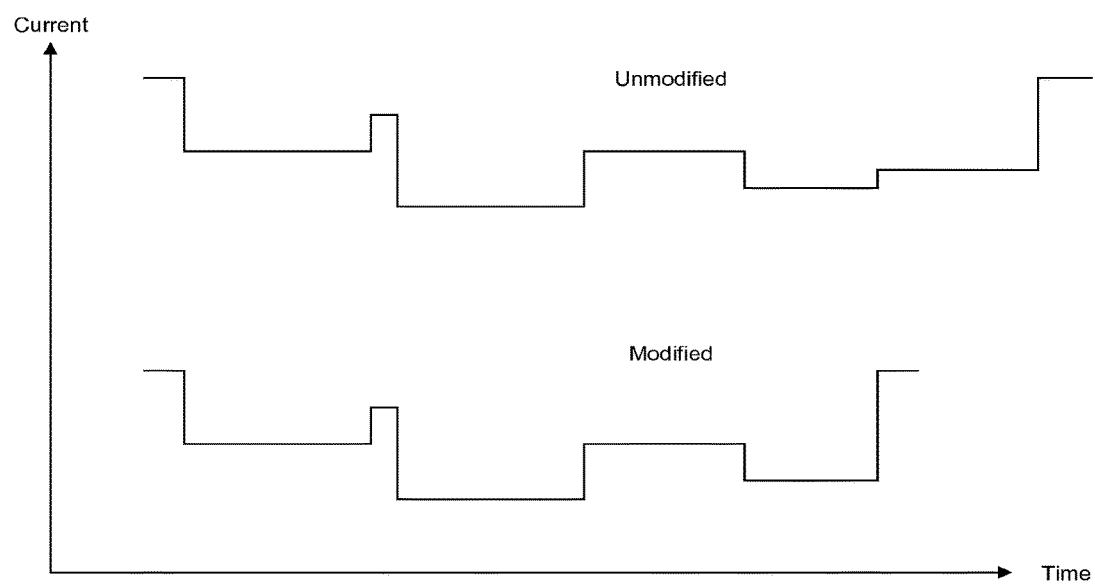

FIG. 4A is an illustration of a FLAP endonuclease assay in which a FLAP probe and a 3-prime region of the target probe are adjacently hybridized to a target polynucleotide. The target probe, FLAP probe, and target polynucleotide form a FLAP substrate in which the target probe is cleaved by a FLAP endonuclease to release the 5-prime region of the target probe. In the illustrated embodiment, the target probe comprises a signal generating segment that displays a unique signal profile to clearly distinguish a coded molecule with and without the signal generating segment. FIG. 4B symbolically illustrates a current blockade signal profile for an unmodified coded molecule and a coded molecule cleaved by a FLAP endonuclease. FLAP endonuclease modification results in release of the 5-prime region of the target probe and loss of the associated signal generating segment.

Figure 5A:
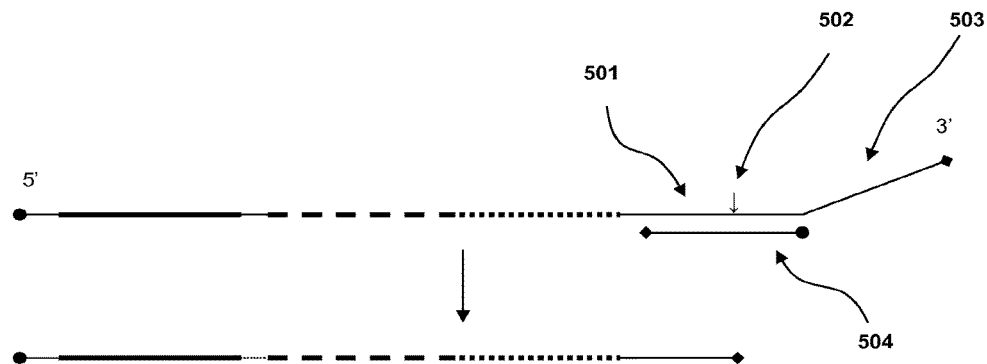
Figure 5B:
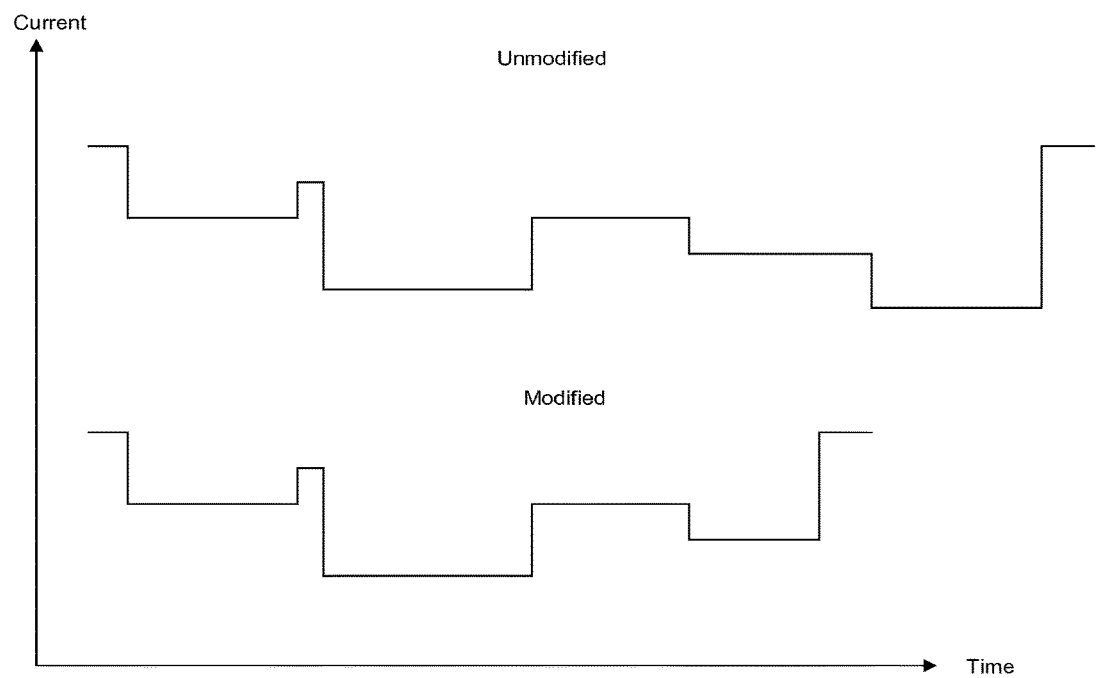

FIG. 5A is an illustration of a sequence or mismatch specific endonuclease assay in which the target probe and the target polynucleotide hybridize to form a recognition site for the sequence-specific or mismatch specific endonuclease. In the illustrated embodiment, the target probe has attached a signal generating segment that generates a unique signal to clearly distinguish a coded molecule with and without the signal generating segment. FIG. 5B symbolically illustrates a current blockade signal profile for an unmodified coded molecule and a coded molecule modified by a sequence-specific or a mismatch specific endonuclease. Cleavage by the endonuclease results in release of a portion of the target probe and its associated signal generating segment.

5. DETAILED DESCRIPTION

It is to be understood that both the foregoing general description, including the drawings, and the following detailed description are exemplary and explanatory only and are not restrictive of this disclosure. In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting.

It is to be further understood that where descriptions of various embodiments use the term "comprising," those skilled in the art would understand that in some specific instances, an embodiment can be alternatively described using language "consisting essentially of" or "consisting of."

The section headings used herein are for organizational purposes only and not to be construed as limiting the subject matter described.

5.2 Definitions

As used throughout the instant application, the following terms shall have the following meanings:

"Nucleobase" or "Base" means those naturally occurring and synthetic heterocyclic moieties commonly known in the art of nucleic acid or polynucleotide technology or polyamide or peptide nucleic acid technology for generating polymers that can hybridize to polynucleotides in a sequence-specific manner. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobases include those nucleobases illustrated in FIGS. 2(A) and 2(B) of Buchardt et al. (WO 92/20702 or WO 92/20703). Nucleobases can be linked to other moieties to form nucleosides, nucleotides, and nucleoside/tide analogs.

"Nucleoside" refers to a compound consisting of a purine, deazapurine, or pyrimidine nucleoside base, e.g., adenine, guanine, cytosine, uracil, thymine, 7-deazaadenine, 7-deazaguanosine, that is linked to the anomeric carbon of a pentose sugar at the 1' position, such as a ribose, 2'-deoxyribose, or a 2',3'-di-deoxyribose. When the nucleoside base is purine or 7-deazapurine, the pentose is attached at the 9-position of the purine or deazapurine, and when the nucleoside base is pyrimidine, the pentose is attached at the 1-position of the pyrimidine (see, e.g., Kornberg and Baker, 1992, *DNA Replication,* 2nd Ed., Freeman. The term "nucleotide" as used herein refers to a phosphate ester of a nucleoside, e.g., a mono-, a di-, or a triphosphate ester, wherein the most common site of esterification is the hydroxyl group attached to the C-5 position of the pentose. "Nucleotide 5'-triphosphate" refers to a nucleotide with a triphosphate ester group at the 5' position. The term "nucleoside/tide" as used herein refers to a set of compounds including both nucleosides and/or nucleotides.

"Nucleobase polymer" or "Nucleobase oligomer" refers to two or more nucleobases that are connected by linkages that permit the resultant nucleobase polymer or oligomer to hybridize to a polynucleotide having a complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide or peptide nucleic acids. Nucleobase polymers or oligomers can vary in size from a few nucleobases, from 2 to 40 nucleobases, to several hundred nucleobases, to several thousand nucleobases, or more.

"Polynucleotides" or "Oligonucleotides" refers to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof. The term nucleic acid encompasses the terms polynucleotide and oligonucleotides and includes single stranded and double stranded polymers of nucleotide monomers.

"Polynucleotide analog" or "Oligonucleotide analog" refers to nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. No. 6,013,785 and U.S. Pat. No. 5,696,253 (see also, Dagani, 1995, *Chem Eng News* 4-5: 1153; Dempey et al., 1995, *J Am Chem Soc* 117:6140-6141). Such positively charged analogues in which the sugar is 2'-deoxyribose are referred to as "DNGs," whereas those in which the sugar is ribose are referred to as "RNGs." Specifically included within the definition of poly- and oligonucleotide analogs are locked nucleic acids (LNAs; see, e.g., Elayadi et al., 2002, *Biochemistry* 41:9973-9981; Koshkin et al., 1998, *J Am Chem Soc* 120:13252-3; Koshkin et al., 1998, *Tetrahedron Letters*, 39:4381-4384; Jumar et al., 1998, *Bioorganic Medicinal Chemistry Letters* 8:2219-2222; Singh and Wengel, 1998, *Chem Commun* 12:1247-1248; WO 00/56746; WO 02/28875; and WO 01/48190; all of which are incorporated herein by reference in their entireties) and nucleic acids with sugar-phosphates other than deoxyribose- or ribose-phosphate backbone, for example, hexopyranosyl-phosphate backbones (Eschenmoser, 1999, *Science* 284:2118-2124).

"Polynucleotide mimic" or "Oligonucleotide mimic" refers to a nucleobase polymer or oligomer in which one or more of the backbone sugar-phosphate linkages is replaced with a sugar-phosphate analog. Such mimics are capable of hybridizing to complementary polynucleotides or oligonucleotides, or polynucleotide or oligonucleotide analogs or to other polynucleotide or oligonucleotide mimics, and may include backbones comprising one or more of the following linkages: positively charged polyamide backbone with alkylamine side chains as described in U.S. Pat. No. 5,786,461; U.S. Pat. No. 5,766,855; U.S. Pat. No. 5,719,262; U.S. Pat. No. 5,539,082; and WO 98/03542 (see also, Haaima et al., 1996, *Angewandte Chemie Int'l Ed. in English* 35:1939-1942; Lesnick et al., 1997, *Nucleosid Nucleotid* 16:1775-1779; D'Costa et al., 1999, *Org Lett* 1:1513-1516 see also Nielsen, 1999, *Curr Opin Biotechnol* 10:71-75); uncharged polyamide backbones as described in WO 92/20702 and U.S. Pat. No. 5,539,082; uncharged morpholino-phosphoramidate backbones as described in U.S. Pat. No. 5,698,685, U.S. Pat. No. 5,470,974, U.S. Pat. No. 5,378,841 and U.S. Pat. No. 5,185,144 (see also, Wages et al., 1997, *Bio Techniques* 23:1116-1121); peptide-based nucleic acid mimic backbones (see, e.g., U.S. Pat. No. 5,698,685); carbamate backbones (see, e.g., Stirchak and Summerton, 1987, *J Org Chem* 52:4202); amide backbones (see, e.g., Lebreton, 1994, *Synlett* 1994:137); methylhydroxyl amine backbones (see, e.g., Vasseur et al., 1992, *J Am Chem Soc* 114:4006); 3'-thioformacetal backbones (see, e.g., Jones et al., 1993, *J Org Chem* 58:2983); sulfamate backbones (see, e.g., U.S. Pat. No. 5,470,967); and α-threofuranosyl backbones (Schoning et al., *Science* 2901347-1351). All of the preceding publications are incorporated herein by reference.

"Peptide Nucleic Acid" or "PNA" refers to poly- or oligonucleotide mimics in which the nucleobases are connected by amino linkages (polyamide backbone) such as described in any one or more of U.S. Pat. Nos. 5,539,082; 5,527,675; 5,623,049; 5,714,33; 5,718,262; 5,736,336; 5,773,571; 5,766,855; 5,786,461; 5,837,459; 5,891,625; 5,972,610; 5,986,053; 6,107,470; 6,451,968; 6,441,130; 6,414,112; and 6,403,763; all disclosures of which are incorporated herein by reference. The term "peptide nucleic acid" or "PNA" shall also apply to any oligomer or polymer comprising two or more subunits of those polynucleotide mimics described in the following publications: Lagriffoul et al., 1994, *Bioorg Med Chem Lett* 4: 1081-1082; Petersen et al., 1996, *Bioorg Med Chem Lett* 6:793-796; Diderichsen et al., 1996, *Tett. Lett.* 37: 475-478; Fujii et al., 1997, *Bioorg Med Chem Lett* 7:637-627; Jordan et al., 1997, *Bioorg Med Chem Lett* 7:687-690; Krotz et al., 1995, *Tett Lett* 36:6941-6944; Lagriffoul et al, 1994, *Bioorg Med Chem Lett* 4:1081-1082; Diderichsen, U., 1997, *Bioorg Med Chem Lett* 7:1743-1746; Lowe et al., 1997, *J Chem Soc Perkin Trans* 1:539-546; Lowe et al., 1997, *J Chem Soc Perkin Trans* 11:547-554; Lowe et al., 1997, *J Chem Soc Perkin Trans* 1:555-560; Howarth et al., 1997, *J Org Chem* 62:5441-5450; Altmann, K-H et al., 1997, *Bioorg Med Chem Lett* 7:1119-1122; Diederichsen, U., 1998, *Bioorg Med Chem Lett* 8:165-168; Diederichsen et al., 1998, *Angew. Chem. mt. Ed.*, 37: 302-305; Cantin et al., 1997, *Tet Lett* 38:4211-4214; Ciapetti et al., 1997, *Tetrahedron* 53:1167-1176; Lagriffoule et al., 1997, *Chem Eur J* 3:912-919; Kumar et al., 2001, *Org Lett* 3(9):1269-1272; and the Peptide-Based Nucleic Acid Mimics (PENAMs) disclosed in WO 96/04000. Some examples of PNAs are those in which the nucleobases are attached to an N-(2-aminoethyl)-glycine backbone, i.e., a peptide-like, amide-linked unit (see, e.g., U.S. Pat. No. 5,719,262; WO 92/20702; and Nielsen et al., 1991, *Science* 254:1497-1500). All publications are incorporated herein by reference.

"Chimeric oligonucleotide" or "Chimeric polynucleotide" refers to a nucleobase polymer or oligomer comprising a plurality of different polynucleotides, polynucleotide analogs and polynucleotide mimics. For example, a chimeric polymer may comprise a sequence of DNA linked to a sequence of RNA. Other examples of chimeric polymers include a sequence of DNA linked to a sequence of PNA or a sequence of RNA linked to a sequence of PNA.

"Detectable tag" refers to a moiety that, when attached to another molecule, e.g., an oligonucleotide, nucleobase polymer, a target polynucleotide, renders such molecule detectable using known detection methods, e.g., spectroscopic, photochemical, electrochemiluminescent, and electrophoretic methods. A detectable tag may have one or more than one label, including different types of labels. Exemplary tags include, but are not limited to, fluorophores, radioisotopes, nanoparticles, and quantum dots. Such tags allow direct detection of labeled compounds by a suitable detector, e.g., a fluorometer.

"Capture tag" refers to a member of a binding pair that, when attached to another molecule, e.g., a nucleotide, oligonucleotide, nucleobase polymer, a target polynucleotide, allows the isolation of the molecule (i.e., captured) by interaction with the other member of the binding pair. A capture tag may have one or more than one tag, including different types of capture tags. Exemplary capture tags include, among others, biotin, which can be incorporated into nucleic acids (Langer et al., 1981, *Proc Natl Acad Sci USA* 78:6633) and captured using streptavidin or biotin-specific antibodies; a hapten such as digoxigenin or dinitrophenol (Kerkhof, 1992, *Anal Biochem* 205:359-364), which can be captured using a corresponding antibody; a fluorophore to which antibodies can be generated (e.g., Lucifer yellow, fluorescein, etc.); and a metal binding domain (e.g., His tag), which can be captured using a suitable metal ligand. In some embodiments, the capture tag can comprise a specific nucleobase sequence, referred to as a "capture sequence," which can be captured using a "capture probe" having a sequence complementary to the capture sequence.

"Watson/Crick Base-Pairing" refers to a pattern of specific pairs of nucleobases and analogs that bind together through sequence-specific hydrogen-bonds, e.g., A pairs with T and U, and G pairs with C, commonly observed in double stranded nucleic acid.

"Annealing" or "Hybridization" refers to the base-pairing interactions of one nucleobase polymer with another that results in the formation of a double-stranded structure, a triplex structure or a quaternary structure. Annealing or hybridization can occur via Watson-Crick base-pairing interactions, but may be mediated by other hydrogen-bonding interactions, such as Hoogsteen or Reverse-Hoogsteen base pairing.

"Deoxynucleotide triphosphates" or "dNTPs" refer to deoxynucleoside triphosphate precursors, i.e., dATP, dTTP, dGTP, and dCTP, and dUTP.

"Wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

"Sequence variation" as used herein refers to differences in nucleic acid sequence between two nucleic acids. For example, a wild-type structural gene and a mutant form of this wild-type structural gene may vary in sequence by the presence of single base substitutions, deletions and/or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

5.3 Methods of Detecting Target Polynucleotides

The present disclosure provides methods of detecting target polynucleotides by hybridizing coded molecules to the target polynucleotides and modifying the coded molecules with a modifying agent, where the modification is dependent on the presence of a hybridized target polynucleotide. In the embodiments herein, the coded molecule comprises one or more block polymer regions, the characteristics of which can be detected by translocating the coded molecule through a nanopore and detecting a signal associated with the block polymer regions. Generally, the detected signal will vary depending on the length and polymer composition of each block polymer region. The signal pattern or signal profile displayed by a coded molecule as a whole can be used as a signature for the specific coded molecule.

In various embodiments, the modification reaction alters the coded molecule, allowing the coded molecule to be separated from unmodified coded molecules and/or changing the signal pattern of the modified coded molecule to distinguish it from a signal pattern of an unmodified coded molecule. Because the coded molecules in various embodiments can be made single-stranded following the modification, both biological and solid state nanopores selective for single-stranded polymers can be used for interrogating the coded molecule. Multiplex assays for detecting a plurality of different target polynucleotides are made possible by using coded molecules with distinguishable signal patterns generated from different block polymers or different combinations of block polymers used to form the coded molecule. The scope of multiplexing formats are further expanded by employing modification reactions that provide additional signal pattern profiles that assist in distinguishing a modified the coded molecule from an unmodified coded molecule. The large numbers of target polynucleotides analyzable with the described methods can allow the detection of any number of target polynucleotides, including the multiplexed detection of nucleotide sequence variations associated with various diseases and the detection of sequence variations that serve as useful genetic markers.

Generally, the method of detecting a target polynucleotide comprises: a) contacting a coded molecule with a target polynucleotide, wherein the coded molecule comprises one or more block polymers and a target probe capable of hybridizing to the target polynucleotide; and b) modifying the coded molecule with a modifying agent, wherein the modification is dependent on the presence of the target polynucleotide hybridized to the target probe. Presence or absence of the modification indicates the presence or absence of the target polynucleotide in a sample.

The term "target polynucleotide" refers to a defined nucleic acid sequence, the presence or absence of which is being detected. A target polynucleotide can be any nucleobase sequence, as further defined below, including but not limited to, DNA, RNA, and chimeric polynucleotides. The target polynucleotide can be obtained from any biological (e.g., cells, viruses, microbes), environmental (e.g., water, soil, air), or forensic sources. Target polynucleotide also includes any polynucleotide generated by any synthetic method, including any chemical synthetic process and any polynucleotide amplification technique, for example, polymerase chain reaction (PCR), oligonucleotide ligation assay (OLA), ligase chain reaction (LCR. RCA), reverse transcriptase PCR (RT-PCR), invasive cleavage reaction, strand displacement cleavage, rolling circle amplification, and in vitro transcription reaction.

The term "modified" polynucleotide refers to a polynucleotide that is structurally altered, such as by addition of nucleotides to one end of the polynucleotide, cleavage of the polynucleotide, replacement of nucleotides, and/or conjugation to another polynucleotide. Various modifications can be adapted for the disclosed methods, including, among others, extension of a target probe on the coded molecule by a template-dependent polymerase, ligation of a ligation probe to the target probe, and cleavage of the target probe by a nuclease. Each of these modifications is dependent on presence of a target polynucleotide hybridized to the target probe of the coded molecule. In the absence of the target polynucleotide, the modification reaction does not occur or occurs inefficiently such that presence or absence of the modification is indicative of the presence or absence of the target polynucleotide in a sample.

The coded molecules treated with a modifying agent are interrogated by translocating the coded molecule through a nanopore and detecting a signal pattern associated with the coded molecule. In some embodiments, prior to analysis through the nanopore, the coded molecule can be made single stranded to permit translocation of the coded molecule through a nanopore selective for a single-stranded polymer.

The term "translocating" refers to transporting or passing a coded molecule through a nanopore such that the coded molecule is interrogated or scanned from one end of the coded molecule to the other end of the coded molecule. Translocation conditions can be selected so that the coded molecule translocates through the nanopore in a substantially linear manner.

The term "signal pattern" refers to the reproducible signal profile obtained upon interrogation of the coded molecule by translocation through a nanopore and detection of detectable properties of the coded molecule. Signal pattern profile is related to the chemical and physical properties of the polymer(s) that form the coded molecule and the detection method used to interrogate it. Signal characteristics include, among others, the time dependence of the signal, the signal amplitude, and the temporal appearance of a characteristic signal relative to other signals.

In various embodiments, the detected signal pattern is associated to a specific coded molecule. The term "associating" refers to decoding the detected signal pattern and identifying the specific coded molecule represented by that signal pattern. Decoding the detected signal pattern can be done by identifying each element of the signal pattern, for example, the current blockade signal produced by each of the block polymer regions, and determining the specific block polymer regions and their arrangement on the detected polymer to ascertain the specific coded molecule detected. Decoding can be also be performed by comparing the detected signal pattern to a known set of signal patterns for coded molecules used in the assay to determine the specific coded molecule detected.

In various embodiments, the presence of a target polynucleotide can be determined by identifying the specific coded molecule translocated through the nanopore based on the detected signal pattern, and ascertaining any change in the signal pattern indicative of a target polynucleotide dependent modification reaction. In some embodiments, the presence of the target polynucleotide can be determined by isolating the modified coded molecule away from unmodified coded molecules, such as through a capture tag that is attached to the coded molecule in a template dependent manner, and then associating the detected signal pattern to a specific coded molecule, and thus the target probe and corresponding target polynucleotide in the sample. In some embodiments, the presence of a target polynucleotide can be determined via a combination of isolating the modified coded molecule via a capture tag that is attached to the coded molecule in a template dependent manner and then ascertaining any change in the signal pattern of the isolated coded molecule, indicative of a target polynucleotide dependent modification reaction.

5.3.1 Coded Molecules

In various embodiments, the coded molecules for the methods herein comprises polymers with one or more defined regions that produces a defined signal when interrogated by translocation through a nanopore. The polymer can be any type of polymer that can be translocated through a nanopore and detected by any detection method. In some embodiments, the coded molecule comprises a nucleobase polymer, with one or more defined polymer regions that have a detectable property distinguishable from the other portions of the coded molecule. The segment can be distinguished based on, among others, temporal appearance of the signal; signal magnitude; signal duration, signal type (e.g., conductance or tunneling current), or a combination of the forgoing signal characteristics.

In some embodiments, the coded molecule comprises a single chain of a nucleobase polymer. In these embodiments, the coded molecule can be a single-stranded polymer of a polynucleotide, such as a single-stranded DNA, single-stranded RNA, or a single-stranded polynucleotide analog or mimic. In some embodiments where the coded molecule comprises a polynucleotide analog or mimic, any number of nucleobase polymers having a backbone other than sugar phosphate linkages can be used.

Polynucleotide analogs and mimics include those having linkages of sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, positively charged analogue "DNGs" and "RNGs"; positively charged polyamide backbone with alkylamine side chains; uncharged polyamide backbones; uncharged morpholino-phosphoramidate; peptide-based nucleic acid mimic backbones; carbamate backbones; amide backbones; methylhydroxyl amine backbones; 3'-thioformacetal backbones; sulfamate backbones and threofuranosyl backbones. Exemplary single nucleobase polymers include a glycol nucleic acid with an acyclic three carbon propyleneglycolphosphodiester backbone and α-threofuranosyl backbones (Schoning et al., supra), both of which can undergo Watson and Crick base pairing interactions (Zhang et al., 2004, *J. Amer. Chem.* Soc. Epub). Other types of nucleobase polymers will be apparent to the skilled artisan.

The coded molecules can also be chimeric nucleobase polymers, where the single-stranded nucleobase polymer comprises a plurality of different nucleobase polymers, such as different combinations of polynucleotides, polynucleotide analogs and polynucleotide mimics. Non-limiting examples of a chimeric nucleobase polymers include, among others, single-stranded polynucleotides comprising a segment of RNA and a segment of DNA, a segment of RNA and a segment of PNA, or a segment of DNA and a segment of PNA. Other chimeric nucleobase polymers will be apparent to the skilled artisan.

In other embodiments, the coded molecule is polymer comprising a chimera of a single stranded nucleobase and non-nucleobase polymers, where the non-nucleobase polymer regions or linkers connect segments of single-stranded nucleobase polymers. Various synthetic polymers can be used to connect polynucleotide segments together to from a linear polymer chain. Non-limiting examples of such polymers include polyethylene glycol (PEG), polystyrenes, polyacrylic acids, polyacetamides, polyphosphates, and other polymers that do not form Watson and Crick or Hoogsteen base pairs with a nucleobase polymer. The synthetic polymers can be block polymers or block copolymers. A non-limiting example of a composite coded molecule is a single stranded polymer formed with a block polymer of polyethylene glycol and a polymer of deoxypolynucleotides, as described in Sanchez-Quesada et al., 2004, *Angew Chem Int Ed* 43:3063-3067 and Jaschke et al., 1994, *Nucleic Acids Res.* 22(22):4810-4817. Other composite polymers of polynucleotides and non-polynucleotide polymers or linkers are described in, among others, U.S. Patent Application No. 2005/0153926; Greenberg et al., *J Org Chem* 66:7151-7154; and Pon and Yu, 2005, *Nucleic Acids Res.* 33(6):1940-1948; the disclosures of which are incorporated herein by reference.

In various embodiments, the block polymer region of the coded molecule comprises any block polymer that has an associated detectable property. The block polymer can be a block polymer of a purine, purine analog, pyrimidine, or pyrimidine analog. For example, exemplary pyrimidine block polymers include polyC, polyT, and polyU, while exemplary purine block polymer include polyA, polyG, and 2,6-diaminoadenine. In other embodiments, the block polymer region can be a block copolymer, such as an alternating copolymer. The alternating copolymer can be alternating purines, alternating pyrimidines or alternating purine/pyrimidine. An exemplary alternating purine is a region of $(AG)_n$, where n is the number of repeating units, while an exemplary alternating pyrimidine is $(CT)_n$. Exemplary block polymer of alternating purine-pyrimidine is $(AC)_n$, $(AT)_n$, $(GC)_n$, or $(GT)_n$. In other embodiments, the block polymer region can be dinucleotide, trinucleotide, or tetranucleotide repeat sequences, e.g., $-(AG)_n-$, $-(CT)_n$, $-(ATC)_n-$, $-(TTA)_n-$, -(AGTC)n, etc., that produce a defined detectable signal.

In the embodiments herein, any number of block polymer regions can be used to generated the coded molecule. Thus, coded molecule can have at least 1, at least 2, at least 3, at least 5, at least 10, at least 20, at least 30, up to 50 or more block polymer regions. It is to be understood that the number of block polymer regions can be readily defined by those skilled in the art, taking into consideration various factors, which include, among others, block polymer length and detectable characteristics of the block polymer region. In some embodiments, the coded molecule comprises a plurality of block polymer regions, where a plurality refers to two or more.

In some embodiments, the plurality of block polymer regions can comprise a combination of block polymer regions in which the block polymer regions differ in sequence and/or polymer type. For example, in some embodiments, a first block polymer region can be a polypurine G with a deoxyribophosphate backbone while a second block polymer region can be a polypurine G with a peptide nucleic acid backbone. While the two regions are made of the same nucleobase, the differences in the backbone are expected to produce two distinguishable signals when interrogated through the nanopore. As will be apparent to the skilled artisan, any number of combinations of block polymer regions of a particular nucleobase and a polymer backbone can be used to generate a diverse number of coded molecules. Exemplary backbones that can be used to distinguish one block polymer region from another include, PNA backbones, phosphorothioate backbones, deoxyribophosphate backbones, and ribophosphate backbones. Backbones of different isomeric forms, such as Rp and Sp phosphorothioate oligonucleotides can be used to distinguish the block polymer regions (see, e.g., Wilk et al., 2000, *J Am Chem Soc* 122:2149).

The length of the block polymer region can be of any length that is sufficient to produce a detectable signal, and can vary depending on the detection method employed and the property of the block polymer region desired. In various embodiments, the block polymer region can be at least about 5 or more monomer units, about 10 or more monomer units, about 25 or more monomer units, about 50 or more monomer units, about 100 or more monomer units, about 200 or more monomer units, about 500 or more monomer units, about 1000 or more monomer units, up to about 2000 or more monomer units. It is to be understood that the length of the block polymer region can be longer as needed to produce a defined signal.

In some embodiments, two or more of the block polymer regions are separated by a non-block polymer region. The term "non-block polymer region" refers to a polymer region that is not made of the same repeating monomer unit. An exemplary non-block polymer region is a polymer region of a random sequence of nucleobases. Non-block polymer region can show a change in the signal between the block polymer regions, which allows distinguishing one block polymer region from another block polymer region, even if the two block polymer regions have the same signal characteristics. Non-block polymer regions of differing lengths in the same range as those described above for the block polymer regions can be used.

In the coded molecules herein, the block polymer regions are ordered on the coded molecule such that detecting the detectable property generates a defined signal pattern. "Ordered" as used herein refers to a specified spatial arrangement of the block polymer regions on the coded molecule. Any number of block polymer regions can be arranged in various permutations to generate a large number of different coded molecules. For example, block polymer regions with the same detectable property can be positioned at different distances from each other to generate coded molecules in which the variation in time period between signals produced allows differentiating one coded molecule from another coded molecule. In other variations, a set of block polymer regions can be arranged in different spatial arrangements on the single stranded coded molecule to generate a large number of coded molecules based on a limited number of block polymer regions.

In some embodiments, the plurality of block polymer regions is ordered on the coded molecule such that the signal pattern obtained is a symmetric signal pattern. A symmetric signal pattern refers to a generated signal pattern that is substantially identical when the coded molecule is translocated through the nanopore beginning from either end of the coded molecule. In still other embodiments, the plurality of the block polymer regions is ordered on the coded molecule such that the signal pattern obtained is an asymmetric signal pattern. An asymmetric signal pattern refers to a generated signal pattern that is not substantially identical when the coded molecule enters the pore at one end of the molecule as compared to the generated signal pattern when the molecule enters the pore from the other end. Thus, a signal pattern that is asymmetrical allows distinguishing the polarity of the coded molecule translocated through the nanopore.

In various embodiments herein, the coded molecule further comprises a target probe having a region that anneals to a target polynucleotide. The term "target probe" refers to a component of the coded molecule having a region complementary or substantially complementary to a target polynucleotide and which anneals to the target polynucleotide under reaction conditions suitable for the modification reaction. In some embodiments, the target probe is on the same polymer strand as the coded molecule. An exemplary target probe of this type is one in which the coded molecule is a deoxyribonucleotide, and a specific sequence of the deoxyribonucleotide is complementary to the target polynucleotide. In other embodiments, the target probe is attached to the coded molecule indirectly, such as through a linker or by hybridization through a complementary sequence. One exemplary embodiment of indirect attachment is where a target probe is hybridized to the target polynucleotide, modified by the modifying agent, and then attached to the coded molecule for analysis via the region of complementarity between the target probe and the coded molecule. This embodiment generates a coded molecule with a double stranded region, which can be interrogated by translocation through the nanopore of sufficient dimension for passage of the double-stranded segment. Typically, however, the target probe is on the same single polymer forming the coded molecule such that the coded molecule can be interrogated via a nanopore that allows for passage of a single stranded polynucleotide. In some of these embodiments, the nanopore is selective for passage of a single stranded polynucleotide.

In various embodiments, the target probe is modifiable by the various modifying agents described herein. Consequently, the region of the target probed involved in the modification reaction is typically a sugar-phosphate backbone of naturally occurring polynucleotides. These regions include, where appropriate, the terminal regions, such as when the modifying agent is a template dependent polymerase, and/or internal regions subject to recognition and cleavage by a nuclease. In some embodiments, the entire target probe is a polynucleotide with a sugar phosphate backbone (e.g., deoxyribonucleic acid or ribonucleic acid). In other embodiments, the target probe can be a chimeric polynucleotide in which one region is a polynucleotide analog or polynucleotide mimic. An exemplary chimeric target probe of this type is a target probe made of a peptide nucleic acid and a polynucleotide, where the polynucleotide region of the target probe is modified by a template-dependent polymerase. For instance, the region hybridizing to the target polynucleotide can be made of the peptide nucleic acid while the terminal region extended by the polymerase is made of a deoxyribonucleic acid. Other chimeric polynucleotides suitable a target probes will be apparent to the skilled artisan.

In some embodiments, the target probe of the coded molecule can further comprise a signal generating segment, as described in the various embodiments herein. The term "signal-generating segment" refers to a polymer or polynucleotide of any sequence and/or length that provides a distinctive signal to the signal pattern of the coded molecule. Typically, the signal-generating segment does not hybridize to the target polynucleotide, although in some embodiments, the signal generating segment can have a region complementary to the target polynucleotide. The signal generating segment can be from about 10 monomer units or longer, 20 monomer units or longer, 50 monomer units or longer, 100 monomer units or longer, 500 monomer units or longer, up to 1000 monomer units. It is to be understood that in some instances, the signal generating segment can be longer if needed to distinguish a modified coded molecule from an unmodified coded molecule. The sequence of the signal-generating segment can be any sequence that produces a distinct signal when interrogated through the nanopore. In some embodiments, the signal generating segment comprises block polymers, as described for coded molecules. Thus, in some embodiments, the signal generating segment can comprise a second coded molecule.

An illustrative coded molecule with block polymer regions is given in FIG. 1A, which shows a single stranded polymer with a first block polymer region 100, a second block polymer region 102, a third block polymer region 103, and a target probe segment 104. A non-block polymer region 101 separates the first and second block polymer regions, and separates the signals generated by the first and second block polymer regions. A target polynucleotide 105 is hybridized to a complementary region of the target probe. A symbolic representation of current blockade signal pattern associated with the coded molecule is provided in FIG. 1B.

In the methods herein, the coded molecules in its various forms are contacted with the target polynucleotide under suitable conditions to permit annealing of the complementary regions of the target probe and the target polynucleotide. The target probe hybridized to the target probes is then treated with a modifying agent to modify the target probe, thereby altering the structure of the coded molecule. The following sections describe various modifying agents suitable for target polynucleotide dependent modifications of coded molecules.

5.3.2 Modification of Coded Molecules By Target Polynucleotide Dependent Primer Extension In some embodiments, the modification is extension of a terminus of the target probe by the action of a modifying agent, where the extension reaction is dependent on presence of a target polynucleotide hybridized to the target probe. Generally, the modification is target polynucleotide directed elongation of the 3-prime terminal region of the target probe in which the modifying agent is a template-dependent polymerase. In these embodiments, the target probe is designed to hybridize to a portion of the target polynucleotide such that the hybridized target polynucleotide has an unhybridized segment that can support extension of the target probe. For example, the target probe can be designed to have 3-prime terminal sequences that hybridize to a 5-prime region of the target polynucleotide, where the remaining 3-prime portion of the target polynucleotide remains unpaired and serves as a template for extension of the target probe.

The term "elongation" refers to extension of a polynucleotide hybridized to another polynucleotide, and typically occurs by extension of the polynucleotide by incorporation of nucleotide triphosphate precursors by a template-dependent polymerase enzyme. The 3-prime terminal nucleotide of the target probe must be properly base-paired to the complementary nucleotide on the target polynucleotide to be elongated by the polymerase. Thus, in some embodiments, the 3-prime terminal nucleotide of the target probe can be used to interrogate a site of sequence variation in the target polynucleotide, such as a nucleotide polymorphism.

In various embodiments, the elongation reaction is carried out in the presence of one or more nucleotide triphosphates suitable as substrates for the template dependent polymerase. In some embodiments, the elongation reaction is carried out in presence of all four nucleotide triphosphates to maximize the elongation reaction and replicate the strand complementary to the unpaired portion of the target polynucleotide.

In some embodiments, the nucleotide triphosphates can be labeled with a detectable tag, such as a fluorophore, hapten, quantum dot, electron-transfer moiety, or a bulky adduct, and detected by the methods described in U.S. provisional application No. 60/736,960, filed Nov. 14, 2005, incorporated herein by reference. As disclosed therein, the label can also be detected by their effect on current blockade, electron tunneling current, or charge induced field effects. Detection of labeled segments can be enhanced by having all four nucleotide triphosphates labeled with a common detectable tag.

In some embodiments, the nucleotide triphosphates are labeled with a capture tag, which can be used to isolate the modified coded molecule from unmodified coded molecules. Exemplary capture tags include, among others, biotin, (Langer et al., 1981, *Proc Natl Acad Sci USA* 78:6633) which can be captured using streptavidin or biotin-specific antibodies; a hapten such as digoxigenin (Kerkhof, 1992, *Anal Biochem* 205:359-364), which can be captured using an anti-digoxigenin antibody; and a fluorophore (e.g., Lucifer yellow, fluoroscein), which can be captured also with a corresponding antibody. In some embodiments, the capture tag can comprise a specific sequence incorporated into the target polynucleotide and which is attached to the coded molecule by the template dependent polymerase. In other embodiments, the capture sequence can be incorporated into a target polynucleotide by ligation of oligonucleotides or use of primers containing the capture sequence in an amplification reaction. Other capture tags that can be substrates for the polymerase will be apparent to a skilled artisan. The ability to isolate coded molecules modified with a capture tag provides a method of determining the presence or absence of a target polynucleotide since only those coded molecules having the capture tag will have been modified in a target polynucleotide dependent manner. Coded molecules modified with a capture tag can be isolated from unmodified coded molecules and analyzed by translocated through a nanopore.

In some embodiments, the target probe of the coded molecule hybridizes to a region of the target polynucleotide immediately adjacent to the nucleotide base to be identified. In these embodiments, the nucleotide base to be interrogated is the first unpaired base in the target polynucleotide (i.e., template) immediately downstream of the 3-prime terminus of the target probe. Enzymatic extension of the target probe by one nucleotide, catalyzed, for example, by a polymerase, thus depends on correct base pairing of the added nucleotide to the nucleotide base to be identified. In some embodiments, the hybridized target probe can be contacted with a polymerase in presence of four terminators nucleotides (e.g., dideoxynucleotides), each terminator being labeled with a different detectable tag or the same or different capture tags. The duplex of the target probe and the target polynucleotide is contacted with the polymerase under conditions permitting base pairing of a complementary terminator nucleotide so as to incorporate the terminator at the 3-primer terminus of the target probe. Use of chain terminating nucleotides for interrogating single nucleotide positions on a target polynucleotide is described in U.S. Pat. No. 588,819, the disclosure of which is incorporated herein by reference.

Various template-dependent polymerases capable of extending the target probe hybridized to the target polynucleotide can be used as the modifying agent. These include, among others, DNA polymerases and reverse transcriptases. The polymerase must be primer and template dependent. Exemplary polymerases include, among others, *E. coli* DNA polymerase I, "Klenow fragment" of DNA polymerase I, T4 DNA polymerase, T7 DNA polymerase (e.g., Sequenase®), *T. aquaticus* DNA polymerase, and retroviral reverse transcriptase (e.g., MMLV). The choice of a template dependent polymerase and selection of the conditions for efficient hybridization and elongation are well within the skill of those in the art. For example, if the 3-prime terminal nucleotide of the target probe is used to interrogate a site of sequence variation in the target polynucleotide, a polymerase substantially lacking in a proof-reading 3-prime to 5-prime exonuclease can be used to minimize removal of the unpaired nucleotide by the exonuclease. In those embodiments in which the target polynucleotide is RNA, a reverse transcriptase can be used to extend the 3-terminal nucleotide of the target probe of the coded molecule.

An illustration of the polymerase mediated extension assay is given in FIG. 1A and FIG. 1B. The illustrated coded molecule is hybridized to the target polynucleotide such that the 3-prime region of the target polynucleotide 105 remains unpaired. The hybridized 3-terminal region of the target probe is then elongated by a template-dependent polymerase by incorporation of nucleotide triphosphate precursors onto the target probe 106. After rendering the modified coded molecule single stranded, the coded molecule is translocated through a nanopore and scanned to detect its associated signal pattern. A symbolic representation of current blockade signal patterns for an unmodified and modified coded molecules are given in FIG. 1B. Elongation of the coded molecules allows the modified coded molecule to be distinguished from the unmodified coded molecule. Further sensitivity in the reaction can be achieved by use of capture tags in the incorporated nucleotides, which allows isolation of modified coded molecules from unmodified coded molecules.

5.3.3 Modification of a Coded Molecule By Rolling Circle Replication

In some embodiments, the modification used in the methods herein is a polymerase mediated extension reaction in which the target polynucleotide is a sequence on a closed circular nucleic acid to which the target probe of the coded molecule hybridizes. Activity of a polymerase extends the target probe, generating tandem copies of the circular nucleic acid attached to the target probe. This form of primer extension is typically referred to as rolling circle replication and is described in U.S. Pat. Nos. 6,977,153; 6,858,412; 6,797,474; 6,783,943; 6,221,603; and 6,210,884, the disclosures of which are incorporated herein by reference. The closed circular target polynucleotide is generated by ligating an open circle probe (OCP) to which hybridizes a nucleic acid sequence of interest. The OCP is a linear nucleic acid that has a 5-prime phosphate at one end and a 3-prime hydroxyl at the other end such that the two ends are capable of being ligated by a ligase. Two terminal portions present on the OCP have sequences complementary to a nucleic acid sequence of interest. A first terminal portion comprises sequences at the 5-prime phosphate terminal region while the second terminal portion comprises sequences at 3-prime hydroxyl terminal region. The first and second terminal portions hybridize to adjacent segments on the nucleic acid of interest, thereby by forming adjacent (i.e., abutted) 5-prime and 3-prime terminal nucleotides of the OCP that serve as substrates for a ligase. In the absence of the specific nucleic acid of interest, ligation of the OCP does not take place.

The open circle further comprises a primer complement portion to which the target probe on the coded molecule hybridizes. Typically, a single primer complement portion is present on the open circle probe, which allows rolling circle replication to initiate at one site. The primer complement portion can be of any length to support hybridization of the target probe of the coded molecule to the circular target polynucleotide and can be located any where within the open circle probe. There is no limitation on the sequence of the primer complement portion as long it has regions complementary to target probe.

In some embodiments, the open circle probe comprises a capture sequence, which comprises sequences complementary to a capture probe. When the ligated circular probe becomes replicated as part of the coded molecule, the modified coded molecule can be isolated through use of a capture probe that is complementary to the capture tag portion. The open circle probe may have one or more capture tag portions, which may be the same sequence or different sequences. As discussed above, in other embodiments, nucleotide triphosphate precursors labeled with capture tags can also be used to isolate coded molecules having tandem copies of the circular target polynucleotide.

In still other embodiments, the OCP can have additional sequences to generate distinctive signal patterns. Thus the OCP can serve as a signal generating segment or another coded molecule when replicated. In some embodiments, the additional sequences can comprise one or more block polymer regions, which in combination, produce a signal pattern in the manner of a coded molecule. OCPs that produce distinctive signal patterns when interrogated through a nanopore can be used to enhance the multiplexing capabilities of the coded molecules.

Generally, the rolling circle reaction is carried out by hybridizing a nucleic acid of interest to the open circle probe, optionally filling any gaps with a polymerase and nucleotide triphosphates (or by use of a gap oligonucleotide), and ligating the open circle probe to generate a closed circular probe. A coded molecule having a target probe with sequence complementary to the primer complementary portion is hybridized to the closed circle probe, and a polymerase added to extend the 3-prime terminal region of the target probe, where the closed circular probe acts as a template for the polymerase. The product formed is a coded molecule with tandem sequences of the closed circular probe attached to the target probe. Because the product of rolling circle replication is single-stranded, the modified coded molecules can be translocated directly through a nanopore selective for a single-stranded polymer. Steps for rolling circle modification of a coded molecule typically can comprise mixing an OCP with a nucleic acid of interest and incubating the sample mixture under conditions promoting hybridization between the open circle probe and the nucleic acid of interest; mixing a ligase with the OCP-nucleic acid mixture and incubating under conditions promoting ligation of the open circle probe; mixing a coded molecule with the ligation mixture and incubating under conditions that promote hybridization between the target probe and complementary sequence on the ligated open circle probe; and adding a template-dependent polymerase and incubating under conditions promoting replication of the circular target polynucleotide.

DNA polymerases useful in the rolling circle replication will typically be capable of displacing the strand complementary to the template strand, have low or no 5-prime to 3-prime exonuclease activity, and have highly processive characteristics. Strand displacement activity is desirable for synthesizing multiple tandem copies of the ligated OCP while low or absent 5-prime to 3-prime exonuclease activity minimizes destruction of the synthesized strand. Suitable DNA polymerases for rolling circle synthesis, include, among others, bacteriophage φ29 DNA polymerase (U.S. Pat. No. 5,198,543 and U.S. Pat. No. 5,001,050), phage M2 DNA polymerase (Matsumoto et al., 1989, *Gene* 84:247), phage φPRD1 DNA polymerase (Jung et al., 1987, *Proc Natl Acad Sci USA* 84:8287), VENT™ DNA polymerase (Kong et al., 1993, *J Biol Chem* 268:1965-1975), Klenow fragment of DNA polymerase I (Jacobsen et al., 1974, *Eur J Biochem* 45:623-627), T5 DNA polymerase (Chatterjee et al., 1991, *Gene* 97:13-19), PRD1 DNA polymerase (Zhu and Ito, 1994, *Biochim Biophys Acta* 1219:267-276), and T4 DNA polymerase holoenzyme (Kaboord and Benkovic, 1995, *Curr Biol* 5:149-157).

In some embodiments, hybridization of the OCP to the nucleic acid of interest leaves a gap between the two terminal portions of the OCP. The length of the gap can be from 1 or more nucleotides, 5 or more nucleotides, 10 or more nucleotides, 50 or more nucleotides, or 100 or more nucleotides. Gaps that are present when the nucleic acid of interest hybridizes to the open circle probe can be filled with a polymerase in presence of nucleotide triphosphates to generate a product suitable for ligation. Polymerases suitable for filling a gap can be any polymerase capable of acting on the gap, but will generally have low or minimal strand displacement activity to limit displacement of the hybridized portion of the target probe. Suitable gap-filling polymerases include, among others, T7 DNA polymerase (Studier et al., 1990, *Methods Enzymol* 185:60-89), T4 DNA polymerase (Kunkel et al., 1987, *Methods Enzymol* 154:367-382), *Thermus flavus* DNA polymerase (MBR, Milwaukee, Wis.), and Stoffel fragment of Taq DNA polymerase (Lawyer et al., 1993, *PCR Methods Appl* 2(4):275-287; and King et al., 1994, *J Biol Chem* 269(18):13061-13064). In some embodiments, the gap is filled by use of gap filling oligonucleotide, which hybridizes to the nucleic acid of interest in the gap space such that the termini of the gap oligonucleotide is adjacent to the 5-prime terminus and 3-prime terminus of the OPC.

In some embodiments, strand displacement for rolling circle replication can be facilitated through the use of strand displacement factors, which allow use of polymerases lacking strand displacement activity. Exemplary strand displacement factors useful for rolling circle modification of a coded molecule include BMRF1 polymerase accessory subunit, adenovirus DNA-binding protein, herpes simplex viral protein ICP8, single-stranded DNA binding proteins, and helicase enzymes.

An illustrative embodiment of a rolling circle based modification is given in FIG. 2A. The components of the coded molecule are identical to that illustrated in FIG. 1A. The target polynucleotide 200 is a closed circular polynucleotide generated by ligation of an OCP hybridized to a nucleic acid of interest. The target probe is complementary to a primer complementary region 201 of the circular target polynucleotide. Treating the hybridized complex with a template dependent polymerase results in replication of tandem copies 202 of the closed circular target polynucleotide. A corresponding symbolic representation of current blockade signal patterns of the unmodified and modified coded molecules are presented in FIG. 2B. In the illustration, the tandem copies are expected to produce a repeating signal pattern that follows the signal pattern associated with the block polymer regions of the coded molecule.

5.3.4 Modification of Coded Molecules by Target Polynucleotide Directed Ligation In some embodiments, the modification is target polynucleotide dependent ligation of a ligation probe to the target probe. In these embodiments, the modifying agent is a ligase capable of ligating two adjacently hybridized polynucleotides. The term "ligation probe" refers to a polynucleotide capable of hybridizing to a first region of the target polynucleotide adjacent to a second region, where the second region hybridizes to the target probe of the coded molecule. "Adjacent" refers to abutting sequences of the target polynucleotide such that two polynucleotides hybridized to adjacent regions forms a complex in which a terminus of one polynucleotide and the terminus of the other polynucleotide are adjacent to one another (i.e., no nucleotide gap exists between the two termini). In the embodiments herein, hybridization of the target probe and the ligation probe to the adjacent first and second regions on the target polynucleotide forms a complex that can be ligated by a ligase if suitable 5-prime and 3-prime terminal structures are present (e.g., 5-prime phosphate and 3-prime hydroxyl).

In some embodiments, the ligation probe and the target probe can hybridize to the target polynucleotide to leave a gap between the hybridized ligation probe and target probe. As noted above, such gaps can be filled by use of a suitable template dependent polymerase in presence of nucleotide triphosphate precursors suitable as substrates for the polymerase. Polymerase can extend the 3-prime hydroxyl terminus of one of the polynucleotides hybridized to the target polynucleotide to fill in the gap, thereby generating a ligation probe and target probe adjacent to one another on the target polynucleotide. Alternatively, a gap oligonucleotide, as discussed above, can be used to fill in the gap. The use of a combination of ligation probe and gap oligonucleotide (or polymerase) can be used to interrogate the presence or absence of particular sequences in the gap, thereby providing another basis for distinguishing the presence or absence of a target polynucleotide.

In some embodiments, the length and/or sequence of the ligation probe is chosen to distinguish the signal pattern of a coded molecule modified by ligation of the ligation probe from the signal pattern of an unmodified coded molecule. In some embodiments, the portion of the ligation probe complementary to the target polynucleotide can be made sufficiently long to produce a signal pattern that distinguishes the ligation probe modified coded molecule from an unmodified coded molecule. In various embodiments, the ligation probe can be from about 10 nucleotides or longer, about 20 nucleotides or longer, about 50 nucleotides or longer, about 100 nucleotides or longer, about 200 nucleotides or longer, up to about 500 nucleotides or more as necessary. It is well within the knowledge of the skilled artisan to determined the length of ligation probe suitable for the purposes herein.

In some embodiments, the ligation probe, in addition to a region complementary to the target probe, has a second region that functions as a signal generating segment. As discussed above, the signal-generating segment can be any polymer or polynucleotide of any sequence and length that distinguishes the signal pattern of the modified coded molecule from the signal pattern of an unmodified coded molecule.

In other embodiments, the ligation probe comprises a label, which may be a detectable tag and/or capture tag. Capture tags can be used to isolate the coded molecule modified by the modifying agent before being analyzed in the nanopore. Detectable tags can be used to detect the modified coded molecule. As discussed herein, detectable tags that can be used, include, among others, fluorophores, nanoparticles, quantum dots, steric modifiers, and electron transfer labels. Detection of the detection tags can use techniques described in U.S. provisional application No. 60/736,960, filed Nov. 14, 2006, incorporated herein by reference.

In various embodiments, the terminal nucleotide of either the target probe or the ligation probe can be used to interrogate a site of nucleotide variation in target molecules based on the inability of ligases to ligate two adjacent polynucleotides in which at least one of the abutting terminal nucleotides is not complementary to the corresponding nucleotide on the target polynucleotide. In some embodiments, the target probe interrogates a site of nucleotide polymorphism on the target polynucleotide. The terminal nucleotide for interrogating the nucleotide on the target polynucleotide can be a 5-prime or 3-prime terminal nucleotide of the target probe. When the interrogating nucleotide is the 5'-terminal nucleotide of the target probe, the ligation probe is designed to hybridize to the target polynucleotide such that the 3-prime terminus of the ligation probe is adjacent to the 5-prime terminus of the target probe. When the interrogating nucleotide is the 3'-terminal nucleotide of the target probe, the ligation probe is designed to hybridize to the target polynucleotide such that 5-prime terminus of the ligation probe is adjacent to the 5-prime terminus of the target probe. In either case, non-complementarity (i.e., a mismatch) between the nucleotide on the target polynucleotide and the interrogating terminal nucleotide of the target probe inhibits ligation of the ligation probe to the target probe.

In other embodiments, the terminal nucleotide of the ligation probe, rather than the target probe, interrogates a site of nucleotide variation on the target polynucleotide. In these embodiments, the interrogating nucleotide can be a 5-prime or 3-prime terminal nucleotide of the ligation probe. When the interrogating nucleotide is the 5-prime terminal nucleotide of the ligation probe, the target probe is designed to hybridize to the target polynucleotide such that the 3-prime terminus of the target probe is adjacent to the 5-prime terminus of the ligation probe. When the interrogating nucleotide is the 3-prime terminal nucleotide of the ligation probe, the target probe is designed to hybridize to the target polynucleotide such that the 5-prime terminus of the target probe is adjacent to the 3-prime terminus of the ligation probe. In either case, non-complementarity of the opposing nucleotide on the target polynucleotide and the interrogating terminal nucleotide of the ligation probe can inhibit the ligation of the ligation probe to the target probe.

In the forgoing embodiments, the modifying agent for the ligation reaction is a ligase. "Ligase" useful for the purposes herein refers to molecules that covalently link polynucleotides adjacently hybridized to the target polynucleotide but that fails or is otherwise inefficient in ligating free ends of a single-stranded polynucleotide. Ligases can be chemical or enzymatic. Enzymatic ligases include, among others, ATP dependent DNA ligases, NADPH dependent DNA ligases, and RNA ligases. Exemplary ligases include, among others, T4 DNA ligase, *E. coli*. DNA ligase (Panasnko et al., 1978, *J Biol Chem*. 253:4590-4592), AMPLIGASE™. (Kalin et al., 1992, *Mutat Res* 283(2):119-123); Winn-Deen et al., 1993, *Mol Cell Probes* 7(3):179-186), *Thermus aquaticus* DNA ligase (Barany, 1991, *Proc Natl Acad Sci USA* 88: 189-193), *Thermus thermophilus* DNA ligase, *Thermus scotoductus* DNA ligase, and *Rhodothermus marinus* DNA ligase (Thorbjarnardottir et al., 1995, *Gene* 151:177-180). T4 DNA ligase is suited for ligations involving RNA due to its ability to ligate DNA ends involved in DNA:RNA hybrids. DNA ligase and RNA ligase ligates DNA strands hybridized to a RNA strand (see, e.g., U.S. Pat. No. 6,368, 801). T4 RNA ligase joins a 3-prime hydroxyl terminated RNA to a 5-prime phosphate terminated RNA (Silber et al., 1972, *Proc Natl Acad Sci USA* 69:3009). RNA molecules hybridized to RNA or DNA strands can be ligated by T4 RNA ligase.

Various chemical ligases can use reactive groups to join two adjacently hybridized polynucleotides. Chemical ligation is described in Naylor and Gilham, 1966, *Biochemistry* 5:2722-2728; Sokolova et al, 1988, *FEBS Lett* 232:153-155; Shabarova, 1988, *Biochimie* 70:1323-1334; Chu, 1988, *Nucleic Acids Res*. 16:3671-3691; Luebke and Dervin, 1991, *J Am Chem Soc* 113:7447-7448; Luebke and Dervan, 1992, *Nucleic Acids Res*. 20:3005-3009; Prakash and Kool, 1992, *J Am Chem Soc* 114:3523-3527; Gryaznov and Letsinger, 1993, *J Am Chem Soc* 115:3808-3809; Gryaznov and Letsinger, 1993, *Nucleic Acids Res*. 114:9197-9198; and U.S. Pat. No. 5,681,943.

An illustrative ligation assay is provided in FIG. 3A. The coded molecule is essentially the same as that described for FIG. 1A. The target polynucleotide 301 comprises adjacent first and second regions while the ligation probe comprises a 5-prime region 300 that hybridizes to the first region of the target polynucleotide. The target probe comprises a 3-prime region 303 that hybridizes to the second region of the target polynucleotide such that the 5-prime terminus of the ligation probe and the 3-prime terminus of the target probe are adjacent when the ligation probe and the target probe are annealed to the target polynucleotide. The ligation probe can further comprise a signal generating segment 305. Upon treatment of the mixture with ligase, the ligation probe 302 is joined to the target probe. The modification results in a coded molecule with a signal pattern distinguishable from the signal pattern of an unmodified coded molecule by the presence of signals contributed by the ligation probe and the signal generating segment. FIG. 3B symbolically illustrates a current blockade signal pattern for a coded molecule modified by ligation of a ligation probe and its corresponding unmodified coded molecule.

In some embodiments, detecting a plurality of different target polynucleotides can use coded molecules that have distinguishable signal patterns, as further described below. In these embodiments, each of the different coded molecules is associated with a target probe that hybridizes to a specific target polynucleotide. Upon interrogating the coded molecule by translocation through a nanopore, the detected signal pattern is decoded and associated to a specific coded molecule and its target probe. In some embodiments, the presence of a target polynucleotide is determined by isolating modified coded molecules from unmodified molecules through use of captures tags on the ligation probes. In other embodiments, a change in the detected signal pattern as compared to a signal pattern of an unmodified coded molecule can be used as the basis for determining the presence of the target polynucleotide. As will be apparent to the skilled artisan, both approaches can be used to increase the sensitivity of detecting a target polynucleotide.

In other embodiments, the same coded molecules can be used but in combination with different ligation probes, where each different ligation probe changes the signal pattern of the coded molecule uniquely to allow a coded molecule modified with one ligation probe to be distinguished from a coded molecule modified with another ligation probe. In some embodiments, the coded molecules can hybridize to the same sequence on different target polynucleotides while the ligation probes hybridize to sequences that vary between the different target polynucleotides. In one exemplification, a first ligation probe can comprise a first signal generating segment and a second ligation probe comprise a second signal generating segment, where the first and second signal generating segment alters the signal pattern of a coded molecule differently (i.e., generates differing first signal pattern and second signal pattern). Detection of both modified signal patterns indicates the presence of first and second target polynucleotides in a sample, while detection of only one of the modified signal pattern indicates presence of only one of the target polynucleotides. Multiplex detection of a plurality of different target polynucleotides can use a plurality of ligation probes in which each ligation probe alters the signal pattern of a coded molecule differently and each ligation probe hybridizes to a different target polynucleotide.

5.3.5 Modification of Coded Molecules by FLAP Endonucleases

In some embodiments for detecting a target polynucleotide, the target probes are designed to be substrates for a FLAP endonuclease. FLAP endonuclease based assays are described in U.S. Pat. Nos. 5,846,717; 5,888,780; 5,985,557; 5,994,069; 6,001,567; 6,090,543; and 6,348,314, the disclosures of which are incorporated herein by reference. In these embodiments, the target probe forms part of a FLAP structure that is a substrate for a FLAP endonuclease (see, e.g., Harrington and Lieber, 1995, *J Biol Chem* 270(9):4503-4508). The term "FLAP structure" generally refers to a structure comprising (a) a target polynucleotide, wherein the target polynucleotide has adjacent first and second regions, (b) a 5-prime polynucleotide probe comprising a 3-prime region and a 5-prime region located immediately 5-prime to the 3-prime region, wherein the 3-prime region is specifically hybridized to the first region of the target polynucleotide, and (c) a 3-prime polynucleotide probe comprising a 5-prime region specifically hybridized to the second region of the target polynucleotide such that the 3-region of the 5'-prime polynucleotide probe and the 5-prime region of the 3-prime polynucleotide probe are specifically hybridized adjacently to the first and second regions of the target polynucleotide. The 5-prime region of the 5-prime polynucleotide probe is an unpaired region, either through strand displacement arising from hybridization of the 3-prime polynucleotide probe, the non-complementarity of the 5-prime region to the target polynucleotide, and/or lower $T_m$ of the 5'-prime region for the target polynucleotide as compared to the 5-prime region of the 3-prime polynucleotide probe. In some embodiments, the 5-prime region of the 5-prime polynucleotide probe is non-complementary to the target polynucleotide.

In the various embodiments herein, the target probe of the coded molecule functions as the 5-prime polynucleotide probe while a FLAP probe acts as the 3-prime polynucleotide probe. The 5-prime region of the target probe is cleaved off by a FLAP endonuclease or other related cleavase enzymes. Thus, for various embodiments based on FLAP structures, the method of detecting a target polynucleotide comprises (a) contacting a target polynucleotide with a target probe having a 5-prime region and a 3-prime region, wherein the target polynucleotide comprises adjacent first and second regions, and wherein the 3-prime region of the target probe is capable of hybridizing to the second region of the target polynucleotide, (b) contacting the target polynucleotide with an FLAP probe, wherein the FLAP probe comprises a 5-prime segment capable of hybridizing to the first region of a target polynucleotide such that the 5-prime segment of the FLAP probe and the 3-prime region of the target probe are adjacently hybridized to the target polynucleotide to form a FLAP substrate, and c) treating with a FLAP endonuclease, wherein the FLAP endonuclease is capable of recognizing the FLAP substrate and cleaves off the 5-prime region of the target probe. Cleavage of the 5-prime region of the target probe separates a portion of the target probe away from the coded molecule, and thereby provide a basis for altering the signal pattern of the modified coded molecule.

In some embodiments, the FLAP structure is a single FLAP structure. A "single FLAP structure" refers to a FLAP structure having a single unpaired region formed by the 5-prime region of the 5-prime polynucleotide probe when hybridized to the target polynucleotide. The 3-prime polynucleotide probe in the single FLAP structure has its 5-prime region specifically hybridized to the first region of the target polynucleotide such that there is no unpaired region on the 3-prime polynucleotide probe overlapping with the 5-prime unpaired region of the 5-prime polynucleotide probe.

In other embodiments, the FLAP structure is a double FLAP structure (Harrington and Lieber, supra). A "double FLAP structure" refers to a FLAP structure in which the 3-prime polynucleotide probe comprises a 3-prime region located immediately 3-prime to a 5-prime region, wherein the 3-prime region of the 3-prime polynucleotide probe is unpaired and overlaps with the unpaired 5-prime region of the 5-prime polynucleotide probe in the FLAP structure. Thus, the double FLAP structure has two unpaired regions, one formed by hybridization of the 5-prime polynucleotide probe and another formed by hybridization of the 3-prime polynucleotide probe, where the two unpaired regions in the double FLAP structures overlap with one another. These double FLAP structures are shown to serve as more efficient substrates for FEN endonucleases as compared to the single FLAP structures, even when the unpaired portion on the 3-prime polynucleotide probe is a single nucleotide (Harrington and Lieber, supra; Kaiser et al., 1999, *J Biol Chem.* 274:21387-21394).

In some embodiments, the double-stranded FLAP structure comprises a FLAP probe having a single unpaired nucleotide in the 3-prime region, such that a single unpaired nucleotide overlaps with the 5-prime unpaired region of the 5-prime polynucleotide probe. Besides being efficient substrates for a FLAP endonuclease, these double FLAP structures, when cleaved by a FLAP endonuclease, typically results in a structure in which the terminus of the FLAP probe is adjacent to the cleaved termini of the target probe, and therefore ligatable by a ligase. Consequently, the methods based on these FLAP structures can further comprise treating with a ligase subsequent to treatment with the FLAP endonuclease. As will be apparent from the descriptions herein, the use of a signal generating segment on the FLAP probe can provide additional signals that can be used to distinguish a FLAP modified coded molecule from an unmodified coded molecule when the FLAP probe is ligated to the cleaved target probe.

It is to be understood that the FLAP structures are not limited to the embodiments above. In some embodiments, the FLAP structure is formed by use of a target probe comprising a first, second, third, and fourth region, wherein the first region is located 3-prime and the fourth region is located 5-prime relative to each other. The second and third regions are located between the first and fourth regions and are complementary to each other such that they hybridize to form a hairpin type structure. The first region is adjacent to the second region and hybridizes to a target polynucleotide such that the target polynucleotide has its 3-prime terminus adjacent to the third region of the target probe to form a FLAP substrate. The fourth region forms the 5-prime unpaired portion in the FLAP substrate, which is cleaved off by a FLAP endonuclease. As noted above, in some embodiments, a 3-prime region of the target polynucleotide can have an unpaired region to form a double FLAP structure.

In the FLAP substrates based on a hairpin type structure, the target polynucleotide can be any polynucleotide being detected, including a 5-prime polynucleotide fragment released from another FLAP substrate. Use of two FLAP reactions in which the first FLAP cleavage detects a nucleic acid of interest and a second FLAP cleavage detects the cleavage product of the first FLAP cleavage reaction can increase the sensitivity of the assay since multiple cycles of hybridization and cleavage can be used to amplify the number of cleaved 5-prime polynucleotide regions available for forming the second FLAP substrate. Such biplex FLAP reactions are described in Lyamichev et al., 1999, *Nat. Biotechnol.* 17:292-296 and Hall et al., 2000, *Proc Natl Acad Sci USA* 97:8272-8277, the disclosures of which are incorporated herein by reference.

In the embodiments herein, various FLAP endonucleases can be used to cleave the FLAP substrates formed with the target probe, the target polynucleotide, and where appropriate, the FLAP probe. The term "FLAP endonuclease" refers to nucleases that recognize FLAP structures and are known to cleave off the unpaired 5-prime region of the 5-prime polynucleotide probe (e.g., target probe). FLAP endonucleases are also known in some embodiments as FEN-1 (Five' ExoNuclease or Flap EndoNuclease) and "structure specific 5'-exonucleases." While not being bound by any theory of action, the FEN-1 nucleases appear to participate in DNA damaged fragment excision, recombinational mismatch correction, and processing of Okazaki fragments during lagging strand DNA synthesis. The endonuclease recognizes and cleaves a double stranded branched nucleic acid structure containing a single-stranded 5-prime flap at the junction where the two strands of duplex DNA adjoin the single-stranded arm. The FEN-1 nucleases, however, do not appear to act efficiently on bubble substrates, 3-prime single-stranded flaps, heterologous loops, and Holliday junctions. FEN-1 endonucleases obtained from natural sources typically have an associated 5-prime to 3-prime exonuclease activity, which can remove RNA primers during lagging strand synthesis and damaged DNA fragments in various DNA repair pathways. Based on protein sequence comparison and biochemical assays, two major conserved motifs, the N (N-terminal) and I (intermediate) motifs, correlate with nuclease activities of FEN-1 type FLAP endonucleases. The FLAP endonuclease activity is not affected by the flap sequence and is generally independent of the 5-prime flap length, cleaving a 5-prime flap as small as one nucleotide. FLAP endonucleases are described for, among others, human (P39748; Harrington and Lieber, supra); chimpanzee (XM_508480.1 GI:55636162); dog (XM_533271.2 GI:73983482); mouse (NM_007999.3 GI:47132513; Karanjawala et al., 2000, *Microb Comp Genomics* 5(3):173-7; Emoto et al., 2005, *Gene* 357 (1):47-54); rat (NM_053430.1 GI:16758169; Kim et al., 2000, *Biochim Biophys Acta* 1496(2-3):333-340); *Xenopus laevis* (Kim et al., 1998, *J Biol Chem* 273(15):8842-8; Bibikova et al., 1998, *J Biol Chem* 273(51):34222-9.); zebra fish (AY391423.1 GI:37362213); *Drosophila melanogaster* (NP_523765.1 GI:17647423; Ishikawa et al., 2004, *Nucleic Acids Res* 32 (21):6251-6259); *Caenorhabditis elegans* (NP_491168.1 GI:17510005) *Saccharomyces cerevisiae* (Harringtone and Lieber, supra); *Schizosaccharomyces pombe* (Alloeva and Doetsch, 1998, *Nucleic Acids Res* 26(16):3645-50); archae (Shen et al., 1998, *Trends Biochem Sci* 23(5):171-3; Hwang et al., 1998, *Nat Struct Biol* 5(8):707-13; Hosfield et al., 1998, *J Biol Chem* 273(42):27154-27161; Collins et al., 2004, *Acta Crystallogr D Biol Crystallogr* 60(9):1674-8); Matsui et al., 1999, *J Biol Chem* 274(26):18297-309; and Kaiser et al., 1999, *J Biol Chem* 274(30):21387-21394), *Oryza sativa* (Kimura et al., 2003, *Gene* 314:63-71); phage T5 (Patel et al., 2002, *J Mol Biol* 320(5):1025-35); *Arabidopsis thaliana* (NP_850877.2 GI:42570539); and cauliflower (Kimura et al., 1997, *Nucleic Acids Res* 25(24):4970-6). All publications incorporated herein by reference.

In other embodiments, the FLAP endonucleases are cleavase agents based on various modified polymerases that recognize and cleave the FLAP structures. Generally, these modified polymerases have a 5-prime nuclease activity but reduced or absent polymerase synthetic activity. FLAP endonucleases of this type have been described for *Thermos aquaticus, Thermos flavus, Thermos thermophilus*, and Cleavase™ (see, e.g., U.S. Pat. No. 5,541,321 and U.S. Pat. No. 5,614,402).

An illustrative example of a FLAP substrate assay is given in FIG. 4A. The coded molecule in the FLAP assay is similar to the coded molecule described for FIG. 1A, except that the orientation is reversed with respect to the 5-prime and 3-prime termini. The FLAP structure comprises a target polynucleotide 403, which has adjacent first and second regions. The target probe has a 3-prime region 400 that is complimentary to the first region of the target polynucleotide, and has an unpaired 5-prime region 401, which in the illustrated embodiment, comprises a signal generating segment. A FLAP probe 402 is hybridized to the second region of the target polynucleotide via a 5-prime region such that the 3-prime region of the target probe and the 5-prime region of the FLAP probe are adjacent to one another when hybridized to the target polynucleotide. Upon treatment with a FLAP endonuclease, the target probe is cleaved off, thereby resulting in separation of the 5-prime region of the target probe from the coded molecule. FIG. 4B symbolically illustrates current blockade signal pattern of a FLAP endonuclease-modified coded molecule and the signal pattern of an unmodified coded molecule. Loss of the 5-prime region of the target probe alters the signal pattern of the FLAP endonuclease modified coded molecule as compared to the signal pattern of an unmodified coded molecule.

As discussed herein, detection of a plurality of different target polynucleotide can be based on used of a plurality of different coded molecules in which each coded molecule has a detectable signal pattern distinguishable from the other coded molecules. Upon interrogating the coded molecule by translocation through a nanopore, the detected signal pattern is decoded and associated to a specific coded molecule and its target probe. Typically, the FLAP endonuclease cleavage site is after the first or second nucleotide in the hybridized duplex formed by the 3-prime polynucleotide probe in the FLAP structure (see, e.g., Kaiser et al., 1999, *J Biol Chem* 274(23):21387-21394). The presence of a gap between the hybridized 5-prime polynucleotide probe and the 3-prime polynucleotide probe (i.e., the two hybridized probes are not abutted to each other), for example because of a nucleotide mismatch in 3-prime region of the 5-prime polynucleotide probe, results in inefficient cleavage by the FLAP endonuclease. As such, in some embodiments, the target probe is used to interrogate a site of nucleotide sequence variation on the target polynucleotide.

In other embodiments, the FLAP probe, rather than the target probe, is used to interrogate a site of nucleotide polymorphism on the target polynucleotide. In these embodiments, the 3-prime nucleotide of the 3-prime region of the FLAP probe interrogates a position of sequence variation in a target polynucleotide. As above, the presence of a mismatch generates a gap between the hybridized FLAP probe and the 3-prime region of target probe such that the substrate is not efficiently recognized and cleaved by the FLAP endonuclease.

In various embodiments, the 5-prime region of the target probe cleaved by the FLAP endonuclease can have a capture tag, such as a capture sequence or biotin ligand, which allows the unmodified coded molecule to be separated from the modified coded molecule because of the removal of the capture tag in a FLAP endonuclease-modified coded molecule.

5.3.6 Modification of Coded Molecules by a Sequence Specific or Mismatch Specific Nuclease In some embodiments, hybridization of the target probe to the target polynucleotide forms an endonuclease recognition site that is recognized by an endonuclease, which cleaves the target probe, thereby modifying the coded molecule. As such, in these embodiments, the modifying agent is an endonuclease that specifically recognizes the endonuclease recognition site. The endonuclease recognition site can be a specific nucleotide sequence and/or a polynucleotide structure. A sequence specific endonuclease recognizes a sequence formed in the hybrid. For example, restriction endonucleases, such as Type II restriction endonucleases, cleave double stranded DNAs on one or both strands of the duplex DNA by recognizing a specific nucleotide sequence, which can be asymmetric or palindromic. On the other hand, structure specific endonucleases recognize a conformation, such as a mismatched nucleotide pair in a duplex, although there can be some effect on endonuclease activity by the type of nucleotide mismatch or the sequences surrounding the mismatch.

In the embodiments above, the method generally comprises hybridizing a target probe to a target polynucleotide to generate a recognition site for an endonuclease and a corresponding endonuclease cleavage site, and treating the hybridized polynucleotides with an endonuclease that recognizes the recognition site and cleaves the hybridized target probe. In some embodiments, the recognition site formed is a sequence specific endonuclease recognition site and the modifying agent is a sequence specific endonuclease that recognizes the recognition site and cleaves the target probe. Removal of a portion of the target probe from the coded molecule can alter the signal pattern, which can be used to discern the presence or absence of a target polynucleotide.

The choice of the sequence-specific endonuclease is dependent on the recognition site that is generated upon hybridization of the target probe to the target polynucleotide. Recognition sites for various types of restriction endonucleases useful for the purposes herein, include, among others, Type I, Type II, and Type III restriction endonucleases (Pingoud and Jeltsch, 2001, *Nucleic Acids Res.* 29(18) 3705-3727). In some embodiments, the target polynucleotide detected comprises a site of restriction site polymorphism, which refers to an endonuclease recognition site that is present in one target polynucleotide but is lacking in a second target polynucleotide. Typically, restriction site polymorphisms are present on target polynucleotides obtained from the same segment of the chromosome in different members of the same species. This sequence variation forms the basis for restriction fragment length polymorphism (RFLP) used for genotyping analysis. Because of its specificity, restriction site polymorphisms based on Type II restriction enzyme recognition sequences are frequently used for genotyping analysis, and can be adapted to the methods herein.

In other embodiments, the endonuclease recognition site formed by hybridization of the target probe to the target polynucleotide is a nucleotide mismatch, which is recognized by a mismatch-specific endonuclease. A "nucleotide mismatch" refers to the pairing of non-complementary bases when a target polynucleotide hybridizes to another polynucleotide. A single nucleotide mismatch is present when a target polynucleotide and another polynucleotide are complementary except for a single non-complementary base-pair. Mismatches can result from pairing of a purine with another purine (e.g., A paired with A, G paired with G, A paired with G), a pyrimidine with another pyrimidine (e.g., C paired with C, C paired with T, and T paired with T), and a pyrimidine with a purine (e.g., C paired with A, and T paired with G). In the embodiments herein, the presence of target polynucleotides is detected by hybridizing a target probe to a target polynucleotide and treating with an endonuclease that recognizes any mismatches, which leads to cleavage of the target probe if a mismatch is present. Perfect complementarity between the target probe and the target polynucleotide does not lead to modification of the target probe.

Various mismatch recognizing endonucleases and mismatch repair systems have been described (see, e.g., U.S. Pat. No. 5,869,245) and can be used for the methods herein. The Mut system is mismatch detection system found in some prokaryotes, which in *E. coli.* comprises proteins MutH, MutS, and MutL (Smith et al., 1996, *Proc Natl Acad Sci USA* 93:4374-4379). The MutS protein recognizes a mismatch and associates with MutL to form a complex that activates the latent endonuclease activity of MutH. MutH cleaves on one side of the mismatch at a hemi-methylated (GATC) sequence and must be activated by MutS and MutL to cleave the DNA. Similar systems have been identified in yeast and mammalian cells and can be adapted for the methods herein.

Another useful mismatch endonuclease is *E. coli.* vsr endonuclease, which recognizes G:T base-pair mismatches in double-stranded DNA within the sequence (CC[A/T]GG) and initiates a repair pathway by hydrolyzing the phosphate group 5-prime to the incorrectly paired T (Turner and Connelly, 2000, *J Mol Biol.* 304(5):765-78). In other embodiments, the mismatch endonuclease is Uvelp, which recognizes all potential DNA base mispair combinations. This endonuclease, found in *Schizosaccharomyces pombe*, recognizes and cleaves DNA 5-prime to the mispaired base in a strand-specific manner. (Kauer et al., 1999, *Mol Cell Biol* 19(7):4703-4710). Uvelp exhibits strong cleavage at the *C/C, *C/A, and *G/G sites; moderate cleavage at *G/A, *A/G, and *T/G sites, and weak cleavage at *G/T, *A/A, *A/C, *C/T, *T/T, and *T/C sites (* indicates the cleaved strand in the mismatch). Thus, Uvelp is useful for detecting most types of mismatches formed between the target probe and the target polynucleotide.

Other types of mismatch endonucleases with broad specificity can be obtained from plants, such as celery. Plant mismatch endonucleases of this type are characterized by an activity with a neutral pH optima and are capable of detecting destabilized regions of DNA helices, such as at a site of a mismatch (Olekowski et al., *Nucleic Acids Res* 26(20): 4597-4602). An exemplary embodiment of a plant mismatch endonuclease is CEL-1 from celery, a mismatch endonuclease that recognizes base substitution mismatched substrates and cuts on one of the two DNA strands for each mismatch duplex. The activity of CEL 1 can be enhanced by the presence of Taq DNA polymerase.

In various embodiments, the length of the target probe cleaved from the coded molecule can be such that the modification alters the signal pattern of the modified coded molecule. The length of the target polynucleotide can be varied, with or without adjusting the length of the region complementary to the target polynucleotide. Thus in some embodiments, the target probe can have a non-complementary region, such as a signal generating segment, that is cleaved off by action of the endonuclease.

An illustrative embodiment of a sequence-specific or structure specific endonuclease assay is provide in FIG. 5A. The target probe 501 hybridizes to a target polynucleotide 504 to generate an endonuclease recognition site 502. In the illustrated embodiment, the endonuclease cleavage site is included within the endonuclease recognition site. Upon treatment with an endonuclease, the target probe is cleaved at the endonuclease cleavage site, thus separating a portion of the target probe from the coded molecule and modifying the signal pattern of the coded molecule. In the illustrated embodiment, the target probe further comprises a signal generating segment 503 to distinguish the endonuclease modified coded molecule from the unmodified coded molecule. FIG. 5B symbolically illustrates a current blockade signal pattern for an endonuclease-modified coded molecule and the signal pattern of an unmodified coded molecule.

5.3.7 Modification of Coded Molecules by Double Stranded Specific Exonucleases

In some embodiments, the modification is target polynucleotide directed degradation of the target probe. In these embodiments, hybridization of the target probe to a target polynucleotide forms a double stranded segment, which is then treated with a suitable exonuclease having specificity for a double stranded polynucleotide. "Exonuclease" refers to a nuclease that degrades a polynucleotide starting from a terminus of the polynucleotide and progressing inward. Double stranded exonucleases degrade the target probe hybridized to the target polynucleotide, as well as the target polynucleotide if susceptible to degradation, thereby modifying the coded molecule. If a sufficient amount of the target probe is degraded, a signal pattern that differs from a non-degraded coded molecule can be generated. Integrity of the coded molecule, other than target probe portion, can be protected by use of nucleobase polymers resistant to nuclease activity (e.g., polynucleotide analogs having PNA backbones).

In some embodiments, the double-stranded exonuclease is a 5-prime to 3-prime double stranded dependent exonuclease and the target probe comprises a 5-prime terminal region that hybridizes to the target polynucleotide. Suitable 5-prime to 3-prime specific double stranded exonucleases include, among others, λ exonuclease (Higuchi and Ochman, 1989, *Nucl. Acids Res* 17:5865, T4 exonuclease B, T7 gene 6 exonuclease (Engler and Richardson, 1983, *J Biol. Chem* 258, 11197-11205), mammalian DNase IV (also known as FEN-1), exonuclease VI (pol 1 small fragment), and exonuclease VII. Where the 5-prime region of the target probe hybridizes to the target polynucleotide but presents a single-stranded overhang, nucleases acting on the single stranded overhang can be used to make the hybridized complex susceptible to the 5-prime to 3-prime double stranded exonucleases.

In other embodiments, the double-stranded exonuclease is a 3-prime to 5-prime double stranded exonuclease and the target probe comprises a 3-prime terminal region that hybridizes to a target polynucleotide to form a double stranded polynucleotide. Exemplary exonucleases of this type include, among others, exonuclease III (also referred to as AP endonuclease VI) and 3-prime to 5-prime nuclease activity of DNA polymerases. As above, where the 3-prime terminal region of the target probe hybridizes to the target polynucleotide but forms a single-stranded overhanging segment, nucleases acting on the single stranded overhang can be used to make the hybridized complex susceptible to the 3-prime to 5-prime double stranded exonuclease.

In some embodiments, the length of the target probe removed by treatment with exonuclease can be varied by adjusting the length of the complementary region between the target probe and the target polynucleotide. In various embodiments, the amount of target probe degraded can be about 10 nucleotides, about 20 nucleotides, about 50 nucleotides, about 100 nucleotides, about 200 nucleotides, about 500 nucleotides, up to about 1000 nucleotides or more. It is well within the skill of those in the art to determine the amount that can be removed from the target probe to alter the signal pattern of the coded molecule.

In some embodiments, where the target polynucleotide is an amplified product, such as PCR product of a nucleic acid of interest, the target polynucleotide can be rendered nuclease resistant, thus limiting the nuclease mediated degradation to the target probe. In still other embodiments, the target probe can be a chimeric polynucleotide in which one region is nuclease resistant while another region is susceptible to the nuclease. Such chimeric target probes can provide a specific endpoint for degradation, thereby providing a well defined signal pattern for the modified coded molecule.

5.3.8 Multiplexing Formats

The methods of detecting a target polynucleotide described in the foregoing sections are adaptable for use in multiplex formats to detect a plurality of different target polynucleotides in a single reaction. In some embodiments, coded molecules with differing signal patterns are used for multiplexed detection, where each coded molecule with a distinguishable signal pattern has a target probe that is complementary to a sequence of a specific target polynucleotide. The plurality of different coded molecules are contacted with a sample, and treated with a modifying agent that modifies the coded molecule in a target polynucleotide dependent manner. Coded molecules are then translocated through a nanopore to detect a signal pattern, which is associated to a specific coded molecule and thus the target polynucleotide detected by that coded molecule. As noted herein, in some embodiments, the modified coded molecule can be isolated away from unmodified coded molecules via a capture tag on the coded molecule prior to translocation through a nanopore, either to increase the sensitivity of the detection or to eliminate the need to determine a change in the signal pattern of the coded molecule.

In various embodiments, the multiplexing method comprises: contacting at least a first coded molecule and a second coded molecule with a plurality of target polynucleotides, wherein (i) the first coded molecule comprises a first one or more block polymer regions and a first target probe capable of hybridizing to a first target polynucleotide, wherein the first coded molecule has a detectable first signal pattern, and (ii) the second coded molecule comprises a second one or more block polymer regions and a second target probe capable of hybridizing to a second target polynucleotide, wherein the second coded molecule has a detectable second signal pattern distinguishable from the first signal pattern. Following treatment with a modifying agent that modifies the first and second target probes when target polynucleotides are hybridized to the target probes, the coded molecules are translocated through a nanopore to detect the signal pattern of each coded molecule. The detected signal pattern is associated to the first or second coded molecule to determine the presence or absence of the target polynucleotides.

Similarly, in some embodiments for detecting a plurality of target polynucleotides, a population of coded molecules is contacted with a plurality of target polynucleotides, wherein the population of coded molecules comprises a plurality of subpopulations and each coded molecule of each subpopulation comprises: (i) a plurality of block polymer regions and a target probe capable of hybridizing to a target polynucleotide, wherein the target probe of each subpopulation hybridizes to a different target polynucleotide; and (ii) a detectable signal pattern distinguishable amongst the plurality of subpopulations. The target probe is modified with a modifying agent, wherein the modification is dependent on the presence of a target polynucleotide hybridized to the target probe. The coded molecule is then translocated through a nanopore to detect the signal pattern of each of the coded molecules. As above, the detected signal pattern is associated to a specific subpopulation of coded molecules to determine the presence or absence of a specific target polynucleotide.

In still other embodiments, multiplexed detection of a plurality of different target polynucleotides can be based on modifications that change the signal pattern of the coded molecule, where the change in the signal pattern is different for each different target nucleotide detected. In some embodiments, the multiplexed detection uses a plurality of different ligation probes as discussed above, where each ligation probe hybridizes to a different target polynucleotide and each ligation probe has a distinguishable signal pattern. In these embodiments, the distinguishable signal pattern of the ligation probes, such as that formed by a signal generating segment, can be used to differentiate the detection of one target polynucleotide from another target polynucleotide.

In other embodiments, the multiplexed detection uses elongation of the 3-prime terminal region of a target probe in a rolling circle replication assay. In these embodiments, a plurality of different circular target polynucleotides (i.e., ligated open circle probes (OPC)) can be used, where each circular target polynucleotide has a distinguishable signal pattern and each hybridizes with a different nucleic acid of interest in forming the ligated OCP. Detecting a specific signal pattern associated with the replicated circular target polynucleotide indicates the presence or absence of a specific circular target polynucleotide and thus the presence or absence of a specific nucleic acid of interest.

In still other embodiments, various coded molecules with differing signal patterns can be used in combination with modifications that provide different signal generating segments, such as with ligation probes or rolling circle templates, to generate a large number of distinguishable signal pattern combinations for detecting a plurality of different target polynucleotides. For instance, if five different SNPs are known to occur for a gene sequence, each occurring at different positions on the gene, five coded molecules with differing signal patterns can be made, one for each SNP site, and combined with five pairs of ligation probes, each pair selective for a normal and variant sequence at one SNP site. Each ligation probe pair can use the same pair of distinguishable signal generating segments, e.g., a first signal generating segment for the ligation probe detecting the normal sequence and a second signal generating segment for the ligation probe detecting the variant sequence. The same pair of signal generating segments can be used for each ligation probe pair since the signal pattern from the combination of the coded molecule and the ligation probe allows differentiation all ten different possible products. As will be apparent from the foregoing, a large number of different combinations can be generated.

5.3.9 Preparation of Coded Molecules, Ligation Probes, and FLAP Probes

The coded molecules, ligations probes, FLAP probes, and other polymers can be made by standard methodologies known in the art. The coded molecule can be synthesized in whole or in parts, where the parts are subsequently joined together. Polynucleotides can be synthesized using standard chemistries, such as phosphoramiditc chemistries (see, e.g., *Current Protocols in Nucleic Acid Chemistry*, John Wiley & Sons, 2003; U.S. Pat. No. 4,973,679; Beaucage, 1992, *Tetrahedron* 48:2223-2311; U.S. Pat. No. 4,415,732; U.S. Pat. No. 4,458,066; U.S. Pat. No. 5,047,524 and U.S. Pat. No. 5,262,530; all of which are incorporated herein by reference). Chimeric polynucleotides, for example chimeras of PNA and DNA, are described in various references, such as U.S. Pat. No. 6,297,016. Synthesis can be carried out using automated synthesizers available commercially, for example the Model 392, 394, 3948 and/or 3900 DNA/RNA synthesizers available from Applied Biosystems, Foster City, Calif.

Methods for synthesizing polynucleotide analogs and mimics will also follow standard methodologies. For example, PNAs are described in U.S. Pat. Nos. 5,539,082; 5,527,675; 5,623,049; 5,714,331; 5,718,262; 5,736,336; 5,773,571; 5,766,855; 5,786,461; 5,837,459; 5,891,625; 5,972,610; 5,986,053; 6,107,470; 6,201,103; 6,350,853; 6,357,163; 6,395,474; 6,414,112; 6,441,130; and 6,451,968; all of which are herein incorporated by reference. General description for PNA synthesis methodologies is given in Nielsen et al., 1999, *Peptide Nucleic Acids; Protocols and Applications*, Horizon Scientific Press, Norfolk England.

Where the coded molecule is a composite of non-nucleobase and nucleobase polymers, the coded molecule can be synthesized in segments and then assembled together or, alternatively, formed by sequential synthesis of the non-nucleobase polymer region and the nucleobase polymer region. For example, phosphoramidite polyethylene glycols along with phosphoramidite nucleotides for synthesis of nucleic acid-PEG composite polymers (Sanchez-Quesada et al., supra) can be used as precursors for synthesizing a composite polymer of polynucleotides and PEG.

Recombinant techniques may also be used to synthesize the coded molecule, or part thereof (see, e.g., Sambrook et al., supra; Ausubel et al., supra). For instance, single-stranded polynucleotides are readily made using single-stranded phage systems by cloning block polymer regions and replicating single-stranded copies of the cloned polynucleotides. Alternatively, polynucleotide sequences forming the coded molecule can be inserted into an appropriate expression vehicle, i.e., a vector which contains the necessary elements for transcription (e.g., T4 or T7 RNA polymerase systems), or in the case of an RNA viral vector, the necessary elements for replication of the RNA. The expression vehicle is then transfected into a suitable host cell which can express the nucleic acid, or used in in vitro transcription systems for synthesis of the desired polynucleotide. Depending on the expression system used, the expressed polynucleotide is then isolated by procedures well-established in the art. Methods for recombinant production of polynucleotides are well established and can be found in standard references such as Sambrook et al., 2001, *Molecular Cloning A Laboratory Manual*, $3^{rd}$ Ed., Cold Spring Harbor Laboratory, N.Y.; and Ausubel et al., 1989, *Current Protocols in Molecular Biology*, Greene Publishing Associates and Wiley Interscience, N.Y., updates to 2005, the disclosures of which is incorporated herein in its entirety.

5.4 Nanopore Devices

In the present disclosure, detecting the coded molecules is carried out by translocating the coded molecule through a nanopore or nanochannel. As used herein, a "pore" or "channel" refers to an orifice, gap, conduit, or groove of sufficient dimension that allows passage or analysis of a single coded molecule. In some embodiments, the nanopore or channel is dimensioned for translocation of not more that one coded molecule at a time. Thus, the dimensions of the nanopore in some embodiments will typically depend on the dimensions of the coded molecule to be examined. A code molecule with a double-stranded region can require a nanopore dimension greater than those sufficient for translocation of a coded molecule which is entirely single-stranded. In addition, presence of detectable tags or capture tags can require larger pores or channels than coded molecules lacking such tags. Typically, a pore of about 1 nm diameter can permit passage of a single stranded polymer, while pore dimensions of 2 nm diameter or larger will permit passage of a double-stranded nucleic acid molecule. In some embodiments, the nanopore or nanochannel is selective for a single stranded coded molecule (e.g., from about 1 nm to less than 2 nm diameter) while in other embodiments, the nanopore or nanochannel is of a sufficient diameter to permit passage of double stranded polynucleotides (e.g., 2 nm or larger). As noted above, it is to be understood that the pore or channel dimensions may be larger where the detection method sufficiently discriminates single coded molecules passing through the pore and/or where the coded molecule has dimensions larger than a double-stranded polynucleotide. For example, for detection based on electron tunneling, the detection region is spatially within a few nanometers of the coded molecule such that the pore or channel is not much larger than the coded molecule itself. However, some detection techniques do not require nanometer proximity of the coded molecule to the detection region and may be capable of detecting a single coded molecule even when the pore, conduit, channel or groove is significantly larger than that required for electron tunneling detection (see, e.g., U.S. Pat. No. 6,413,792 and U.S. published application No. 2003/0211502, incorporated herein by reference).

Various types of nanopore may be used for analyzing the coded molecules. These include, among others, biological nanopores that employ a biological pore or channel embedded in a membrane. Another type of nanodevice is a solid state nanopore in which the channel or pore is made whole or in part from a fabricated or sculpted solid state component, such as silicon.

5.4.1 Biological Pores

For detecting the coded molecules, any biological pore with channel dimensions that permit translocation of the coded molecules can be used. Two broad categories of biological channels are suitable for the methods disclosed herein. Non-voltage gated channel allow passage of molecules through the pore without requiring a change in the membrane potential to activate or open the channel. On the other hand, voltage gated channels require a particular range of membrane potential to activate channel opening. Most studies with biological nanopores have used α-hemolysin, a mushroom-shaped homo-oligomeric heptameric channel of about 10 nm in length found in *Staphylococcus aureus*. Each subunit contributes two beta strands to form a 14 strand anti-parallel beta barrel. The pore formed by the beta barrel structure has an entrance with a diameter of approximately 2.6 nm that contains a ring of lysine residues and opens into an internal cavity with a diameter of about 3.6 nm. The stem of the hemolysin pore, which penetrates the lipid bilayer, has an average inside diameter of about 2.0 nm with a 1.5 nm constriction between the vestibule and the stem. The dimensions of the stem are sufficient for passage of single-stranded nucleic acids but not double-stranded nucleic acids. Thus, α-hemolysin pores may be used as a nanopore selective for singled-stranded polynucleotides and other polymers of similar dimensions.

In other embodiments, the biological nanopore is of a sufficient dimension for passage of polymers larger than a single-stranded nucleic acid. An exemplary pore is mitochondrial porin protein, a voltage dependent anion channel (VDAC) localized in the mitochondrial outer membrane. Porin protein is available in purified form and, when reconstituted into artificial lipid bilayers, generates functional channels capable of permitting passage of double-stranded nucleic acids (Szabo et al., 1998, *FASEB J.* 12:495-502). Structural studies suggest that porin also has a beta-barrel type structure with 13 or 16 strands (Rauch et al., 1994, *Biochem Biophys Res Comm* 200:908-915). Porin displays a larger conductance compared conductance of pores formed by α-hemolysin, maltoporin (LamB), and gramicidin. The larger conductance properties of porin support studies showing that the porin channel is sufficiently dimensioned for passage of double-stranded nucleic acids. Pore diameter of the porin molecule is estimated at 4 nm. The diameter of an uncoiled double-stranded nucleic acid is estimated to be about 2 nm.

Another biological channel that may be suitable for scanning double stranded polynucleotides are channels found in *B subtilis* (Szabo et al., 1997, *J. Biol. Chem.* 272:25275-25282). Plasma membrane vesicles made from *B subtilis* and incorporated into artificial membranes allow passage of double-stranded DNA across the membrane. Conductance of the channels faulted by *B subtilis* membrane preparations is similar to those of mitochondrial porin. Although there is incomplete characterization (e.g., purified form) of these channels, it is not necessary to have purified forms for the purposes herein. Diluting plasma membrane preparations, either by solubilizing in appropriate detergents or incorporating into artificial lipid membranes of sufficient surface area, can isolate single channels in a detection apparatus. Limiting the duration of contact of the membrane preparations (or protein preparations) with the artificial membranes by appropriately timed washing provides another method for incorporating single channels into the artificial lipid bilayers. Conductance properties may be used to characterize the channels incorporated into the bilayer.

In some embodiments, the biological pore may be modified to incorporate a sensing label for sensing the detectable property of the coded molecule, including the sensing of detectable tags incorporated into the coded molecule. Various sensing labels may be used to modify the channel of the biological pore but without significantly affecting the channel dimensions. For example, α-hemolysin has been modified at the pore region by attachment of a short single-stranded nucleotide (via a linker) to a cysteine residue on the hemolysin channel subunit. Pores with modifications to only one of the pore subunits can alter the translocation of single-stranded nucleic acids through the hemolysin pore. Single-stranded molecules that hybridize to the attached nucleobase oligomer display current blockades longer in duration than single-stranded nucleic acids that are not complementary to the attached nucleobase oligomer (Howorka et al., 2001, *Nature Biotechnol.* 18:1091-5).

For generating the biological nanopores, proteins capable of forming the channels can be isolated from natural sources or made by recombinant methods (Szabo et al., supra; Sambrook et al., supra; Ausubel et al., supra). In other embodiments, isolated plasma membrane preparations can be used as the source of the biological pores. Proteins can be reconstituted into artificial membranes and functional channels detected using standard electrophysiological techniques used to measure single channel activity. Methods and apparatus for incorporating biological pores into artificial membranes are described in U.S. Pat. No. 6,267,872, incorporated herein by reference.

5.4.2 Solid State Pores

In other embodiments, analysis of the coded molecules is carried out by translocating the coded molecule through a nanopore or nanochannel fabricated from non-biological materials. Nanopores or channels can be made from a variety of solid state materials using a number of different techniques, including, among others, chemical deposition, electrochemical deposition, electroplating, electron beam sculpting, ion beam sculpting, nanolithography, chemical etching, laser ablation, and other methods well known in the art (see, e.g., Li et al., 2001, *Nature* 412:166-169; and WO 2004/085609). Solid state materials include, by way of example and not limitation, any known semiconductor materials, insulating materials, and metals. Thus, the nanopores may comprise without limitation silicon, silicon, silicon nitride, germanium, gallium arsenide, metals (e.g., gold, silver, platinum), metal oxides, and metal colloids.

To make a pore of nanometer dimensions, various feedback procedures can be employed in the fabrication process. In embodiments where ions pass through a hole, detecting ion flow through the solid state material provides a way of measuring pore size generated during fabrication (see, e.g., U.S. Published Application No. 2005/0126905). In other embodiments, where the electrodes define the size of the pore, electron tunneling current between the electrodes gives information on the gap between the electrodes. Increases in tunneling current indicate a decrease in the gap space between the electrodes. Other feedback techniques will be apparent to the skilled artisan.

In some embodiments, the nanopore is fabricated using ion beam sculpting, as described in Li et al., 2003, *Nature Materials* 2:611-615. In the described process, a layer of low stress silicon nitride film is deposited onto a silicon substrate via low pressure chemical vapor deposition. A combination of photolithography and chemical etching can be used to remove the silicon substrate to leave behind the silicon nitride layer. To form the pore, a focused ion beam (e.g., argon ion beam of energy 0.5 to 5.0 KeV and diameter 0.1 to 0.5 mm) is used to generate a hole in the silicon nitride membrane. By suitable adjustment of the ion beam parameters (e.g., total time the silicon nitride is exposed to the ion beam and the exposure duty cycle) and sample temperature, material can be either removed to enlarge the hole or material added to decrease the hole size. Ion beam bombardment at room temperature and low duty cycle results in migration of material into the hole while bombardment at 5° C. and longer duty cycles results in enlargement of the hole. Measuring the amount of ions transmitted through the pore provides a feedback mechanism for precisely controlling the final pore size (Li et al., supra). To form a nanopore of useful dimensions, a hole larger than the final desired pore dimensions can be made using sculpting parameters that result in loss of the silicon nitride. Subsequently, the size of the pore is adjusted to a dimension suitable for translocation of non-single-stranded polymers using sculpting parameters that result in movement of material into the initially formed hole.

In other embodiments, the nanopores may be made by a combination of electron beam lithography and high energy electron beam sculpting (see, e.g., Storm et al., 2003, *Nature Materials* 2:537-540). A silicon-on-insulator, fabricated according to known methods, is used to form a silicon membrane, which is then oxidized to form a silicon oxide layer. Using a combination of electron-beam lithography and anisotropic etching, the silicon oxide is removed to expose the silicon layer. Holes are made in the silicon by KOH wet etching and the silicon oxidized to form a silicon oxide layer of about 40 nm. Exposure of the silicon dioxide to a high energy electron beam (e.g., from a transmission electron microscope) deforms the silicon dioxide layer surrounding the hole. Whether the initial holes are enlarged or decreased depends on the initial size. Holes 50 nm or smaller appear to decrease in size while holes of about 80 nm or larger increase in size. A similar approach for generating a suitable nanopore by ion beam sputtering technique is described in Heng et al., 2004, *Biophy J* 87:2905-2911. The nanopores are formed using lithography with a focused high energy electron beam on metal oxide semiconductor (CMOS) combined with general techniques for producing ultrathin films.

In other embodiments, the nanopore is constructed as provided in U.S. Pat. Nos. 6,627,067; 6,464,842; 6,783,643; and U.S. Publication No. 2005/0006224 by sculpting of silicon nitride. Initially, a layer of silicon nitride is deposited on both sides of a silicon layer by chemical vapor deposition. Following addition of a photoresist in a manner that leaves a portion of the silicon nitride layer exposed, the exposed silicon nitride layer on one side is removed by conventional ion etching techniques to leave behind a silicon coated with silicon nitride on the other side. The silicon can be removed by any number of etching techniques, such as by anisotropic KOH etching, thus leaving behind a membrane of silicon nitride. The thickness of the silicon nitride membrane is controlled by adjusting the thickness deposited onto the silicon. By use of electron beam lithography or photolithography, a cavity is produced on one side of the silicon nitride layer followed by thinning of the membrane on the other side of the cavity. Suitable thinning processes include, among others, ion beam sputtering, ion beam assisted etching, electron beam etching, and plasma reactive etching. Numerous variations on this fabrication process, for example, use of silicon nitride layer sandwiched between two silicon layers, can be used to generate different nanopores. As noted above, a feedback mechanism based on measuring the rate and/or intensity of ions passing through the pore provides a method of controlling the pore size during the fabrication process.

In still other embodiments, the nanopore can be constructed as a gold or silver nanotube. These nanopores are formed using a template of porous material, such as polycarbonate filters prepared using a track etch method, and depositing gold or other suitable metal on the surface of the porous material. Track etched polycarbonate membranes are typically formed by exposing a solid membrane material to high energy nuclear particles, which creates tracks in the membrane material. Chemical etching is then employed to convert the etched tracks to pores. The formed pores have a diameter of about 10 nm and larger. Adjusting the intensity of the nuclear particles controls the density of pores formed in the membrane. Nanotubes are formed on the etched membrane by depositing a metal, typically gold or silver, into the track etched pores via an electroless plating method (Menon et al., 1995, *Anal Chem* 67:1920-1928). This metal deposition method uses a catalyst deposited on the surface of the pore material, which is then immersed into a solution containing Au(I) and a reducing agent. The reduction of Au(I) to metallic Au occurs on surfaces containing the catalyst. Amount of gold deposited is dependent on the incubation time such that increasing the incubation time decreases the inside diameter of the pores in the filter material. Thus, the pore size may be controlled by adjusting the amount of metal deposited on the pore. The resulting pore dimension is measured using various techniques, for instance, gas transport properties using simple diffusion or by measuring ion flow through the pores using patch clamp type systems. The support material is either left intact, or removed to leave gold nanotubes. Electroless plating technique is capable of forming pore sizes from less than about 1 nm to about 5 nm in diameter, or larger as required. Gold nanotubes having pore diameter of about 0.6 nm appears to distinguish between Ru(bpy)2+2 and methyl viologen, demonstrating selectivity of the gold nanopores (Jirage et al., 1997, *Science* 278:655-658). Modification of a gold nanotube surface is readily accomplished by attaching thiol containing compounds to the gold surface or by derivatizing the gold surface with other functional groups. This features permits attachment of pore modifying compounds as well as sensing labels, as discussed herein. Devices, such as the cis/trans apparatuses used for biological pores described herein, can be used with the gold nanopores to analyze single coded molecules.

Where the mode of detecting the coded molecule involves current flow through the coded molecule (e.g., electron tunneling current), the solid state membrane may be metalized by various techniques. The conductive layer may be deposited on both sides of the membrane to generate electrodes suitable for interrogating the coded molecule along the length of the chain, for example, longitudinal electron tunneling current. In other embodiments, the conductive layer may be deposited on one surface of the membrane to form electrodes suitable for interrogating coded molecules across the pore, for example, transverse tunneling current. Various methods for depositing conductive materials are known, including, sputter deposition (i.e., physical vapor deposition), non-electrolytic deposition (e.g., colloidal suspensions), and electrolytic deposition. Other metal deposition techniques are filament evaporation, metal layer evaporation, electron-beam evaporation, flash evaporation, and induction evaporation, and will be apparent to the skilled artisan.

In some embodiments, the detection electrodes are formed by sputter deposition, where an ion beam bombards a block of metal and vaporizes metal atoms, which are then deposited on a wafer material in the form of a thin film. Depending on the lithography method used, the metal films are then etched by means of reactive ion etching or polished using chemical-mechanical polishing. Metal films may be deposited on preformed nanopores or deposited prior to fabrication of the pore.

In some embodiments, the detection electrodes are fabricated by electrodeposition (see, e.g., Xiang et al., 2005, *Angew. Chem. Int. Ed.* 44:1265-1268; Li et al., *Applied Physics Lett.* 77(24):3995-3997; and U.S. Publication Application No. 2003/0141189). This fabrication process is suitable for generating a nanopore and corresponding detection electrodes positioned on one face of the solid state film, such as for detecting transverse electron tunneling. Initially, a conventional lithographic process is used to form a pair of facing electrodes on a silicon dioxide layer, which is supported on a silicon wafer. An electrolyte solution covers the electrodes, and metal ions are deposited on one of the electrodes by passing current through the electrode pair. Deposition of metal on the electrodes over time decreases the gap distance between the electrodes, creating not only detection electrodes but a nanometer dimensioned gap for translocation of coded molecules. The gap distance between the electrodes may be controlled by a number of feedback processes. In some configurations, the feedback for controlling the distance between the two electrodes uses the potential difference between the two electrodes. As the gap between the electrodes decreases, the potential difference decreases. In other configurations, control of the distance between the two electrodes uses the electron tunneling current across the electrode pair (Li et al, supra). As the distance between the electrodes decrease, electron tunneling current increases. Feedback control using electron tunneling is suitable for fabrication of electrodes with gap distances of about 1 nm or less, while the feedback control based on electrode gap potential allows fabrication of electrodes having gap distances about 1 to about 10 nm. Rate of electrodeposition depends on the electrolyte concentration and the current flowing through the electrodes. Constant current may be used to form layers of metal on the electrodes. In other embodiments, pulses of current may provide precise control over electrode fabrication since pulsed currents can be used to deposit a known number of metal atoms onto the electrodes per each pulse cycle.

Where the detection is based on imaging of charge induced field effects, a semiconductor can be fabricated as described in U.S. Pat. No. 6,413,792 and U.S. published application No. 2003/0211502. The methods of fabricating these nanopore devices can use techniques similar to those employed to fabricate other solid state nanopores. In some embodiments, the field effect detector is made using a silicon-on-insulator that comprises a silicon substrate with a silicon dioxide layer and a p-type silicon layer (doped silicon in which the majority of the charge carriers are positively charged holes). A shallow n-type silicon (doped silicon in which the majority of the charge carriers are negatively charged holes) layer is formed in the p-type silicon layer by ion implantation and addition of an n-type dopant, while another n-type silicon layer that extends through the p-type silicon layer is formed on another region of the silicon-on-insulator. Removal of the silicon substrate and silicon dioxide layers by etching exposes the p-type silicon on the face opposite to the first formed shallow n-type layer. On the newly exposed face of the p-type silicon, a second shallow n-type silicon layer is formed, which connects to the n-type silicon layer that extends through the p-type silicon layer. For interrogating the coded molecules, a nanopore that extends through the two shallow n-type silicon layers and the p-type silicon layer is generated by various techniques, for example by ion etching or lithography (e.g., optical or electron beam). To decrease the nanopore size, a silicon dioxide layer can be formed by oxidizing the silicon. Metal layers are attached to the first formed n-type silicon layer and the n-type silicon layer that extends through p-type silicon, thereby forming the source and drain regions. Detection of the coded molecule, and where suitable, the target polynucleotide, is carried out as further described below.

For analysis of the coded molecules, the nanopore may be configured in various formats. In some embodiments, the device comprises a membrane, either biological or solid state, containing the nanopore held between two reservoirs, also referred to as cis and trans chambers (see, e.g., U.S. Pat. No. 6,627,067). A conduit for electron migration between the two chambers allows electrical contact of the two chambers, and a voltage bias between the two chambers drives translocation of the coded molecule through the nanopore biological nanopores. A variation of this configuration is used in analysis of current flow through biological nanopores, as described in U.S. Pat. Nos. 6,015,714 and 6,428,959; and Kasianowiscz et al., 1996, *Proc Natl Acad Sci USA* 93:13770-13773, the disclosures of which are incorporated herein by reference.

Variations of the device above is disclosed in U.S. application publication no. 2003/0141189. A pair of nanoelectrodes fabricated by electrodeposition are positioned on a substrate surface. The electrodes face each other and have a gap distance sufficient for passage of a single nucleic acid. An insulating material protects the nanoelectrodes, exposing only the tips of the nanoelectrodes for the detection of the nucleic acid. The insulating material and nanoelectrodes separate a chamber serving as a sample reservoir and a chamber to which the polymer is delivered by translocation. Cathode and anode electrodes provide an electrophoresis electric field for driving the coded molecule from the sample chamber to the delivery chamber.

The current bias used to drive the coded molecule through the nanopore can be generated by applying an electric field directed through the nanopore. In some embodiments, the electric field is a constant voltage or constant current bias. In other embodiments, the movement of the coded molecule is controlled through a pulsed operation of the electrophoresis electric field parameters (see, e.g., U.S. Pat. Application No. 2003/141189 and U.S. Pat. No. 6,627,067). Pulses of current may provide a method of precisely translocating one or only a few bases of a coded molecule for a defined time period through the pore and to briefly hold the nucleic within the pore, and thereby provide greater resolution of the electrical properties of the coded molecule.

The nanopore devices may further comprise an electric or electromagnetic field for restricting the orientation of the coded molecule as it passes through the nanopore. This holding field can be used to decrease the movement of the coded molecule within the pore. Variations in the position of the coded molecule in the nanopore can increase the background noise of the detected signal. For instance, when current blockade is measured, movement of the coded molecule within the pore is likely to result in variations of current flow depending on the position of the coded molecule in the pore. Similarly, where the detection measures electron tunneling current, the current signal is likely to be sensitive to the spatial orientation of the coded molecule relative to the detection electrodes. Movement of the coded molecule, for instance through random Brownian motion, would generate variability in the signal measured, which may create complexities in assigning a signal pattern to a specific coded molecule. By holding or restricting the orientation of the coded molecule as it translocates through the nanopore, variations in the detected signal can be minimized.

In some embodiments, an electric field that is orthogonal to the direction of translocation is provided to restrict the movement of the coded molecule within the nanopore. This is illustrated in U.S. Application Publication No. 2003/0141189 through the use of two parallel conductive plates above and beneath the sample plate. These electrodes generate an electric field orthogonal to the direction of translocation of a coded molecule, and thus holding the coded molecule to one of the sample plates. A negatively charged backbone of a DNA, or nucleic acid modified to have negative charges on one strand, will be oriented onto the anodic plate, thereby limiting the motion of the coded molecule. Analogous use of an orthogonal electric field to hold a nucleic acid in a limited orientation for detection is described in U.S. Pat. No. 6,627,067. Electrodes positioned to generate an electric field orthogonal to an extended nucleic acid are used to hold the nucleic acid in a groove, where the nucleic acid is interrogated with a probe (e.g., electron tunneling probe). Similar to the control of the electric field for moving the coded molecule through the nanopore, the orthogonal electric field may be controlled in regard to the duration and amplitude of the holding field. The electric field used for translocation is coordinated with the electric field used to hold the DNA in a restricted orientation to precisely control the movement of a nucleic acid through the nanopore.

In still other embodiments, controlling the position of the coded molecule is carried out by the method described in U.S. Application Publication No. 2004/0149580, which employs an electromagnetic field created in the pore via a series of electrodes positions near or on the nanopore. In these embodiments, one set of electrodes applies a direct current voltage and radio frequency potential while a second set of electrodes applies an opposite direct current voltage and a radio frequency potential that is phase shifted by 180 degrees with respect to the radio frequency potential generated by the first set of electrodes. This radio frequency quadrupole holds a charged particle (e.g., nucleic acid) in the center of the field (i.e., center of the pore). Holding the translocating coded molecule in the middle of the nanopore is predicted to reduce the variability of electron flow through a pore and may also provide consistency in current flow measured by electron tunneling. It is suggested that altering the amplitude of the radio frequency quadrupole could also be used to force the coded molecule to one side of the nanopore and slow the rate of translocation through the pore.

5.5 Signal Pattern Detection

Interrogating the coded molecule by translocation through a nanopore and detecting the detectable property generates a signal pattern. The combination of the signals from each distinctive region of the coded polymer (e.g., block polymer region, ligated ligation probe, etc.) forms a composite signal pattern that identifies the coded molecule. The type of detection method employed will correspond to the property being detected for the polymers that make up the coded molecule.

In some embodiments, the detectable property is the effect of the coded molecule on the electrical properties of the nanopore as the coded molecule translocates through the pore. Electrical properties of the nanopore include among others, current amplitude, impedance, duration, and frequency. Devices for detecting the pore's electrical properties typically comprises a nanopore incorporated into a thin film or a membrane, where the film or membrane separates a cis chamber and a trans chamber connected by a conducting bridge. The coded molecule to be analyzed is placed on the cis side of the nanopore in an aqueous solution typically comprising one or more dissolved salts, such as potassium chloride. Application of an electric field across the pore using electrodes positioned in the cis and trans side of the nanopore causes translocation of the coded molecule through the nanopore, which affects the migration of ions through the pore, thereby altering the pore's electrical properties. Current is measured at a suitable time frequency to obtain sufficient data points to detect a current signal pattern. The generated signal pattern can then be compared to a set of reference patterns in which each reference pattern is obtained from examination of a single population of known coded molecules. Shifts in current amplitude, current duration, and current magnitude define a signal pattern for the coded molecule. Measurement of current properties of a nanopore, such as by patch clamp techniques, is described in publications discussed above and in various reference works, for example, Hille, B, 2001, *Ion Channels of Excitable Membranes,* 3rd Ed., Sinauer Associates, Inc., Sunderland, Mass.

In some embodiments, the detectable property of the coded molecule is quantum tunneling of electrons. Quantum tunneling is the quantum-mechanical effect of transitioning through a classically-forbidden energy state via a particle's quantum wave properties. Electron tunneling occurs where a potential barrier exists for movement of electrons between a donor and an acceptor. To detect electron tunneling, a microfabricated electrode tip is positioned about 2 nanometers from the specimen. At an appropriate separation distance, electrons tunnel through the region between the tip and the sample, and if a voltage is applied between the tip and the sample, a net current of electrons (i.e., tunneling current) flows through the gap in the direction of the voltage bias. Where the nanodevice uses detection electrodes for measuring tunneling current, the electrodes are positioned proximately to the translocating coded molecule such that there is electron tunneling between the detection electrodes and coded molecule. As further discussed below, the arrangement of the electrodes relative to the translocating coded molecule will dictate the type of electron transport occurring through the coded molecule.

In some embodiments, analysis of the coded molecule involves detecting current flow occurring through the nucleic acid chain (i.e., longitudinally along the nucleic acid chain) (Murphy et al., 1994, *Proc Natl Acad Sci USA* 91(12):5315-9). The exact mechanism of electron transfer is unknown, although electron tunneling is given as one explanation for DNA's transport properties. However, the physics underlying electron transport through a double-stranded nucleic acid is not limiting for the purposes herein, and detection of current flowing through the nucleic acid serves to distinguish one polymer region of the coded molecule from another polymer region, and hence distinguish one coded molecule from another coded molecule. For detection of electron electron flow occurring longitudinally through the coded molecule chain, the detection electrodes are positioned longitudinally to the direction of coded molecule translocation such that there is a gap between the electrodes parallel to the chain of an extended coded molecule. In various embodiments, the detection electrodes may be placed on opposite sides of a layer(s) (e.g., membrane) separating the two sides of the nanopore, while in other embodiments, the detection electrodes may be positioned within the layer(s) that separate the two sides of the nanopore.

Another mode of electron flow in a nucleic acid is that occurring across the nucleic acid, for example, a direction transverse to an extended nucleic acid chain (e.g., across the diameter of a double-stranded nucleic acid). In a double-stranded nucleic acid, electron transport may occur through the paired bases while in a single-stranded nucleic acid, electron transport may occur through a single unpaired base. Furthermore, differences in the chemical compositions, hydration structures, interactions with charged ions, spatial orientation of each base, and different base pairing combinations will alter the transverse electron transport characteristics, and thus provide a basis for distinguishing a coded molecule that differ in sequence and/or polymer backbone. For detection of electron flow across the coded molecule (i.e., transverse to an extended nucleic acid chain), the detection electrodes are positioned on one side of the nanopore to interrogate the coded molecule across rather than through the nanopore.

In embodiments of longitudinal or transverse detection, the thickness of the electrodes may determine the total number of bases interrogated by the electrodes. For transverse detection, the tips of the detection electrodes may be dimensioned to interrogate a single nucleobase, and thereby obtain single base resolution. In other embodiments, the dimensions of the detection electrode are arranged to interrogate more than one nucleobase. Thus, in some embodiments, the number of nucleobases interrogated at any one time may be about 2 or more, about 5 or more, about 10 or more, or about 20 or more depending on the resolution required to detect differences in the various polymer regions of the coded molecule.

In some embodiments, the coded molecule is detected using an electron tunneling probe, such as that used in an electron tunneling microscope. In these embodiments, the electrode tip is rastered across a small region of the sample. As the tip scans the surface, differences in the electron density at the surface of the sample cause corresponding variations in the tunneling current. Changes in tunneling current provide a map of the variations in electron density at the surface of the coded molecule. For the embodiments herein, the coded molecule may be absorbed onto a surface in an extended conformation and then scanned using an electrode tip. In other embodiments, the electrode tip of the electron tunneling microscope is held stationary while the coded molecule is translocated across the tip. A device for translocating a nucleic acid across an electrode probe is described in PCT publication WO 00/79257.

In other embodiments, differences in the structure and spatial orientation of a coded molecule may be detected as differences in capacitance. This type of measurement is illustrated in U.S. application publication no. 2003/0141189. Capacitance causes a phase shift in an applied ac voltage at a defined applied frequency and impedance. Phase shift characteristics for each nucleobase is determined for nucleic acids of known sequence and structure, and used as reference standards for identifying individual base characteristics. Nearest neighbor analysis may permit capacitance measurements extending to more than a single nucleobase.

In other embodiments, the detection technique is based on imaging charge-induced fields, as described in U.S. Pat. No. 6,413,792 and U.S. published application No. 2003/0211502, the disclosures of which are incorporated herein by reference. For detecting coded molecules based on charge induced fields, a semiconductor device described above is used. Application of a voltage between a source region and a drain region results in flow of current from the source to the drain if a channel for current flow forms in the semiconductor. Because each nucleobase has an associated charge, passage of a coded molecule through the semiconductor pore induces a change in the conductivity of the semiconductor material lining the pore, thereby inducing a current of a specified magnitude and waveform. Currents of differing magnitude and waveform are produced by different bases because of differences in charge, charge distribution, and size of the bases. In the embodiments disclosed in U.S. Pat. No. 6,413,792, the polymer passes through a pore formed of a p-type silicon layer. Translocation of the coded molecule is achieved by methods similar to those used to move a polymer through other types of channels, as described above. The magnitudes of the current is expected to be on the order of microampere range, which is much higher than the expected picoampere currents detected by electron tunneling. Because the polymer block regions in the coded molecule comprise more than a single nucleobase, these block polymer regions should produce distinctive signals reflective of the charge and charge distribution of the block polymer regions.

It is to be understood that although descriptions above relate to individual detection techniques, in some embodiments, a plurality of different techniques may be used to examine a single coded molecule (see, e.g., Kassies et al., 2005, *J Microsc* 217:109-16). Examples of multiple detection modes include, among others, current blockade in combination with electron tunneling current, and current blockage in combination with imaging charge induced fields. Concurrent detection with different detection modes may be used to identity a coded molecule by correlating the detection time of the resulting signal between different detection modes.

5.6 Detection of Target Polynucleotides

In various embodiments, the target polynucleotide refers to the polynucleotide detected by the coded molecule. The target polynucleotide can be any nucleobase sequence, including but not limited to, genomic DNA (gDNA), RNA (e.g., mRNA; noncoding RNA, tRNA, siRNA, snRNA), nucleic acid obtained from subcellular organelles (e.g., mitochondria or chloroplasts), and nucleic acid obtained from microorganisms, parasites, or viruses. Furthermore, a target polynucleotide can be present in single-stranded forms, multi-stranded forms (e.g., double-stranded, triple stranded), or a mixture of single-stranded and multi-stranded forms. The target polynucleotides can be linear, circular, or branched.

In some embodiments, the target polynucleotide can be an amplicon generated by any suitable amplification technique including, but not limited to polymerase chain reaction, oligonucleotide ligation assay, ligase chain reaction, reverse transcriptase PCR, invasive cleavage, rolling circle amplification, and strand displacement cleavage reactions (see, e.g., U.S. Pat. Nos. 4,683,195; 4,683,202; 4,800,159; 4,965, 188; 5,075,216; 5,130,238; 5,176,995; 5,185,243; 5,354, 668; 5,386,022; 5,427,930; 5,455,166; 5,516,663; 5,656, 493; 5,679,524; 5,686,272; 5,869,252 6,025,139; 6,040,166; 6,197,563; 6,297,016; 6,514,736; and European Patent Nos. EP0200362, EP0201184, and EP320308). Amplicons suitable for use in the methods and compositions described herein can be obtained from cells, cell lysates, and tissue lysates.

In various embodiments, the samples to be analyzed may be obtained from various sources. "Sample" is to be used in the broad sense and is intended to include a wide range of environmental sources and biological materials, including compositions derived or extracted from such biological materials, such as amplicons described above. Non-limiting examples of environmental samples include food, water, soil, waste, or air. Exemplary biological samples include, among others, whole blood; red blood cells; white blood cells; buffy coat; hair; nails and cuticle material; swabs (e.g., buccal swabs, throat swabs, vaginal swabs, urethral swabs, cervical swabs, throat swabs, rectal swabs, lesion swabs, abcess swabs, nasopharyngeal swabs, and the like); urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, biopsy material, and the like. Tissue culture cells, including explanted material, primary cells, secondary cell lines, and the like, as well as lysates, extracts, or materials obtained from any cells, are also within the meaning of the term biological sample as used herein. Microorganisms and viruses that may be present on or in a sample are also within the scope of the invention. Materials obtained from forensic settings are also within the intended scope of the term sample.

The samples can be used without further processing or processed according to various methods typically used to prepare samples. For instance, samples containing cells or bacteria may be subjected to physical conditions to disrupt the cells and liberate their contents. Non-limiting examples of such techniques include, among others, sonication, pressure, heat, irradiation, and mechanical shearing. Samples may also be treated with detergents, denaturing agents (e.g., guanidinium chloride), chaotropic salts, and enzymes such as lysozymes, nucleases, glycosidases, etc. Samples may be subjected to further manipulation, such as filtration, chromatography, precipitation, solvent extraction, and derivatization.

For detecting the target polynucleotide, the sample is contacted with the coded molecule under conditions suitable for interaction of the target polynucleotide and the binding moiety. Typically, conditions are chosen that minimize non-specific interactions and stabilize annealing between the complementary regions of the target polynucleotide and the target probe. The conditions will vary depending on the type of polynucleotide and may be readily determined by the skilled artisan. Guidance is provided in various reference works, such as Sambrook et al., *Molecule Cloning: A Laboratory Manual,* 3rd Ed., Cold Spring Harbor Laboratory Press (2001), *Current Protocols in Molecular Biology,* Ausubel. F. ed., Greene Pub. Associates (1998) updates to 2005; all publications incorporated herein by reference. Factors for consideration include, among others, incubation time, pH, ionic strength, temperature, and divalent ion concentration. For nucleic acid detection, these conditions can be varied to create a level of hybridization stringency that minimizes hybridization of non-complementary sequences while being stable to complementary target sequences.

In some embodiments, annealing characteristics of a nucleobase polymer can be determined by the $T_m$ of the hybrid complex. The greater the $T_m$ value, the more stable the hybrid. $T_m$ is the temperature at which 50% of a nucleobase oligomer and its perfect complement form a double-stranded oligomer structure. The $T_m$ for a selected nucleobase polymer also varies with factors that influence or affect hybridization. For example, such factors include, but are not limited to, factors commonly used to impose or control stringency of hybridization, (i.e., formamide concentration (or other chemical denaturant reagent), salt concentration (i.e., ionic strength), hybridization temperature, detergent concentration, pH, and the presence or absence of chaotropes. Optimal stringency for forming a hybrid combination can be found by the well-known technique of fixing several of the aforementioned stringency factors and then determining the effect of varying a single stringency factor. The same stringency factors can be modulated to control the stringency of hybridization of a PNA to a polynucleotide, except that the hybridization of a PNA is fairly independent of ionic strength. Optimal or suitable stringency for an assay can be experimentally determined by examination of each stringency factor until the desired degree of discrimination is achieved.

The $T_m$ values for the nucleobase oligomers can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci USA* 83:8893-8897; Freier et al., 1986, *Proc. Natl. Acad. Sci USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, *In Developmental Biology Using Purified Genes* (Brown et al., eds.), pp. 683-693, Academic Press; and Wetmur, 1991, *Crit Rev Biochem Mol Biol* 26:227-259. All publications incorporate herein by reference.

Following hybridization of the target probe to the target probe, the coded molecule and target polynucleotide mixture is treated with a modifying agent as described above for the various embodiments. Conditions for the modification reactions can be standard conditions in which the modifying agents are known to be active. In some embodiments, the coded molecule can be isolated from unmodified molecules, such as through use of capture tags. In addition, prior to translocation of the coded molecule through the nanopore, the coded molecule in some embodiments can be made single-stranded by any of known techniques (e.g., heating, chemical denaturation, etc.) to permit analysis in single-stranded coded molecules.

For detecting a signal pattern, a coded molecule is placed into a nanopore device and then driven or transported into the nanopore using a suitable force, typically a biased electric field. The driving force may be constant or varied in a controlled manner, such as by use of pulsed current. As the coded molecule translocates through the nanopore, the polymer is interrogated to sense the detectable property of the coded molecule. Interrogation of the coded molecule occurs sequentially as it is translocated through the nanopore. By "sensing" or "scanning" refers to the process of evaluating and/or interrogating the detectable property of the coded molecule in an orderly manner. The orientation of the coded molecule may be determined, relative to a reference or orientation point, for example but not limited to, a block polymer region, a detectable tag, or a distinguishable sub-pattern of the signal pattern generated by the code molecule. The signal pattern can then be compared to a reference set of signal patterns to identity the coded molecule sampled and relate or associate its identity to the corresponding target probe and thus the target polynucleotide detected. In some embodiments, each coded molecule identified can be counted to quantitate the amount of a particular target polynucleotide present in a sample.

In various embodiments, the form of the signal pattern depends on which end of the coded molecule enters the nanopore. In order to decode and identify the target probe in a mixture of coded molecule-labeled target probes, the signal pattern of each coded molecule can be unique. This orientation-dependent signal pattern can be addressed in various ways. In some embodiments, the signal patterns of a coded molecule entering the pore in both orientations can be obtained and decoded to associate it with a specific coded molecule. Although this method of associating a particular set of signal patterns to a coded molecule reduces the number of coded molecules that can be devised from a defined set of block polymer regions, the reduction in the number of usable coded molecules can be compensated by simply increasing the number of block polymer regions used in the coded molecule. Block polymer combinations that are expected to produce similar signal patterns in either orientation can be eliminated.

In other embodiments, the orientation of the coded molecule interrogated through the nanopore can be assessed by determining the change in signal pattern of the coded molecule modified by the modifying agent. The modification and corresponding change in signal pattern of the coded molecule effectively serves as a marker for orientation of the coded molecule in the nanopore. By using a modification that results in a unique signal, different from the signal pattern generated when the coded molecule enters the pore through the other orientation, the orientation of the coded molecule can be readily determined. For example, the modification can be ligation probes with different signal generating segments and/or ligation probes of differing nucleotide lengths, which generates an asymmetry in the signal pattern.

As noted above, the coded molecules can be used to detect a variety of target polynucleotides, including, among others, genomic DNA (gDNA); RNA (e.g., mRNA; noncoding RNA, tRNA, siRNA, snRNA); mitochondria or chloroplast DNA; nucleic acid obtained from microorganisms (e.g., fungi, bacteria); parasites (e.g., trypanosomes, nematodes, helminthes); DNA or RNA viruses; and synthetic nucleobase sequences (e.g., sequences for isolating a PCR product). In some embodiments, the target polynucleotide can be from a pathogenic organism, non-limiting examples of which include, among others, *Salmonella, Campylobacter, Vibrio cholerae, Leishmania*, enteric *E. coli*, retroviruses, herpesviruses, adenoviruses, and lentiviruses. In still other embodiments, the polynucleotide probe sequences are directed to variants of a specific pathogen. For instance, drug resistant human immunodeficiency virus (HIV) can arise from mutations in the genes that encode the molecules targeted by anti-retroviral drugs, such as mutations in HIV gene encoding the protease enzyme that renders the protease resistance to protease inhibitors used for HIV therapy. Thus, polynucleotide probe sequences that distinguish the various mutations can be used in the coded molecules to detect protease resistant viral strains.

In some embodiments, the target polynucleotides detected are mutated sequences associated with inherited disorders.

Non-limiting examples include, among others, mutations responsible for cystic fibrosis, hereditary nonpolyposis colorectal cancer, hemophilia, Huntington's disease, leukodystrophy, and sickle cell disease. Different mutations causing each genetic disorder can be detected by use of a pair of coded molecules for each mutation site, where one coded molecule has a target probe for the normal sequence and another coded molecule has a target probe for the mutated sequence.

In still other embodiments, the target polynucleotide detected is associated with a sequence variation within a population. These sequence variations have uses in evolutionary studies, familial relationship analysis, forensic analysis, disease diagnosis, disease prognosis, and disease risk. As used herein, a "polymorphism" is a variation in the DNA sequence in some members of a species. A polymorphism is "allelic," in that, due to the existence of the polymorphism, some members of a species may have the unmutated sequence (i.e., the wild type "allele") whereas other members may have a mutated sequence (i.e., the variant or mutant "allele"). When only one mutated sequence exists, the polymorphism is referred to as "diallelic." In the case of diallelic diploid organisms, three genotypes are possible. The organism can be homozygous for one allele, homozygous for the other allele, or heterozygous. In the case of diallelic haploid organisms, they can have one allele or the other, thus only two genotypes are possible. The occurrence of alternative mutations can give rise to trialleleic, etc. polymorphisms. Allelic polymorphisms referred to as "single nucleotide polymorphisms," or "SNPs" are polymorphism that contains a polymorphic site, "X," which is the site of the polymorphism's variation.

SNPs have several advantages for genotyping. SNPs are more stable than other classes of polymorphisms, and SNPs occur at greater frequency and with greater uniformity over a genetic region, which permits the use of SNPs with tighter linkage to a particular phenotypic trait of interest. An exemplary SNP variation suited for the methods herein are the sequence variation associated with apolipoprotein E (ApoE), which is correlated with an increased risk for Alzheimer's Disease. The ApoE gene displays polymorphisms predominantly at two nucleotide positions that result in three possible alleles for this gene: E2, E3, and E4. Each allele, differing by one base, produces a protein product that differs by one or two amino acids from the other alleles. An individual inheriting at least one e4 allele has an increased risk of developing Alzheimer's while inheriting the E2 allele is not associated with an increased risk.

Another example of useful SNP variations are those associate with cytochrome P450 enzymes, a superfamily of heme containing monooxygenases. Human cytochrome P450 enzyme families, such as CYP1, CYP2, and CYP3, metabolize various drugs and environmental chemicals such that differences in the activities of specific enzymes within each cytochrome P450 family can affect drug metabolism (Gonzalez, F. J., 1992, *Trends Pharmacol Sci* 13(9)346-52). An SNP that results in low or no expression of CYP2C9 can increase the risk of adverse effects of taking tolbutamide or coumadin because of the low metabolism of these drugs in subjects carrying the SNP in the CYP2C9 (Schwarz, U. I., 2003, *Eur J Clin Invest* 33 Suppl 2:23-30). Detecting polymorphisms in these and other drug metabolizing enzymes (e.g., esterases) can be used to predict a subject's response to a drug.

As will be apparent to the skilled artisan based on the guidance herein, uses of the coded molecule in methods above are numerous, and are applicable to detection of target nucleotides other than those specifically described. Furthermore, the multiplexing capabilities of the methods allow its use to detect a large number of different target polynucleotides in a single assay.

5.7 Kits

The coded molecules and devices for their analysis can be provided in the form of kits. The kits can comprise coded molecules for detecting target polynucleotides and corresponding coded molecule reference standards, including unmodified coded molecules and modified coded molecules for comparing signal patterns of test samples. Kits can further include nanopore devices created on a single chip for detecting the coded molecules. In various embodiments, the kits can also include instructions for proper use of the coded molecules and nanopore devices. Instructions and diagrams can be on any medium, non limiting examples of which include, printed forms, magnetic tape, flash memory, compact disc, and magnetic disks.

The foregoing descriptions of embodiments have been presented for purposes of illustration and description and are not intended to be exhaustive or to limit the scope of the disclosure to the precise forms disclosed. The teachings herein are intended to encompass various alternatives, modifications, and equivalents, as will be appreciated by those of skill in the art.

All patents, patent applications, publications, and references cited herein are expressly incorporated by reference to the same extent as if each individual publication or patent application was specifically and individually indicated to be incorporated by reference.

What is claimed is:

1. A method of detecting a target polynucleotide, comprising:
   a) contacting a coded molecule with a target polynucleotide, wherein the coded molecule comprises
      (i) one or more block polymer regions, and
      (ii) a target probe capable of hybridizing to the target polynucleotide;
   b) modifying the target probe with a modifying agent, wherein the modification is dependent on the target polynucleotide hybridized to the target probe; and
   c) translocating the coded molecule through a nanopore and detecting a signal pattern associated with the coded molecule;
   wherein the target polynucleotide comprises adjacent first and second regions, and the target probe comprises a 5-prime region and a 3-prime region, and wherein the method further comprises hybridizing a FLAP probe to the target polynucleotide, wherein the FLAP probe comprises a 3-prime segment that hybridizes to the first region, and the 3-prime region of the target probe hybridizes to the second region such that the 3-prime segment of the FLAP probe and the 3-prime region of the target probe are adjacently hybridized to the target polynucleotide to form a FLAP substrate, and wherein the modifying agent is a FLAP endonuclease and the modification is cleavage of the target probe.

2. The method of claim 1, further comprising the step of rendering the coded molecule single-stranded prior to translocation through the nanopore.

3. The method of claim 1, further comprising comparing the detected signal pattern to a signal pattern of an unmodified coded molecule, wherein a difference in the detected signal pattern of the modified coded molecule compared to the signal pattern of the unmodified coded molecule indicates the presence of the target polynucleotide.

4. The method of claim 1, further comprising associating the detected signal pattern to the target probe.

5. The method of claim 1 in which the 5-prime region of the target probe is non-complementary to the target polynucleotide.

6. The method of claim 1 in which the FLAP probe further comprises a 3-prime unpaired segment that overlaps with the 5-prime region of the target probe in the FLAP substrate, thereby forming a double FLAP substrate.

* * * * *